US009833359B2

(12) United States Patent
Clopp

(10) Patent No.: US 9,833,359 B2
(45) Date of Patent: Dec. 5, 2017

(54) TYMPANOSTOMY TUBE DELIVERY DEVICE WITH CUTTER FORCE CLUTCH

(71) Applicant: Tusker Medical, Inc., Menlo Park, CA (US)

(72) Inventor: Mathew D. Clopp, Santa Clara, CA (US)

(73) Assignee: TUSKER MEDICAL, INC., Menlo Park, CA (US)

( * ) Notice: Subject to any disclaimer, the term of this patent is extended or adjusted under 35 U.S.C. 154(b) by 150 days.

(21) Appl. No.: 14/457,266

(22) Filed: Aug. 12, 2014

(65) Prior Publication Data
US 2016/0045369 A1 Feb. 18, 2016

(51) Int. Cl.
*A61F 11/00* (2006.01)
*A61B 17/34* (2006.01)
(Continued)

(52) U.S. Cl.
CPC ......... *A61F 11/002* (2013.01); *A61B 17/3415* (2013.01); *A61B 17/3468* (2013.01);
(Continued)

(58) Field of Classification Search
CPC .... A61F 11/002; A61F 11/004; A61F 11/006; A61F 11/00; A61B 17/3415; A61B 17/3417; A61B 17/8819; A61B 17/32002; A61B 17/320016; A61B 17/34; A61B 17/3421; A61B 2017/3443; A61B 2017/3445; A61B 2017/3449; A61B 2017/00477; A61B 2017/00787;
(Continued)

(56) References Cited

U.S. PATENT DOCUMENTS 858,673 A 7/1907 Roswell
1,920,006 A 7/1933 Dozier et al.
(Continued)

FOREIGN PATENT DOCUMENTS

CN 86105171 A 3/1987
DE 19618585 11/1997
(Continued)

OTHER PUBLICATIONS

International Search Report and Written Opinion for International Application No. PCT/US2015/044183, dated Nov. 4, 2015.
(Continued)

*Primary Examiner* — Jocelin Tanner

(57) ABSTRACT

A tympanostomy tube delivery device comprises a drive assembly and a force limiting shaft assembly. The shaft assembly comprises a cannula and a piercer operable to translate relative to the cannula so as to pierce the tympanic membrane of a patient. The piercer is mechanically coupled with the drive assembly such that actuation of the drive assembly causes translation of the piercer relative to the cannula. The piercer is mechanically coupled with the drive assembly by a clutch. The clutch is resiliently biased to couple the piercer with the drive assembly. The clutch is configured to uncouple the piercer from the drive assembly in response to a threshold force being imposed upon the piercer so as to inhibit translation of piercer relative to the cannula.

21 Claims, 30 Drawing Sheets

(51) Int. Cl.
*A61B 17/00* (2006.01)
*A61B 90/00* (2016.01)

(52) U.S. Cl.
CPC .............. *A61B 2017/00367* (2013.01); *A61B 2017/00477* (2013.01); *A61B 2017/00787* (2013.01); *A61B 2090/038* (2016.02)

(58) Field of Classification Search
CPC .......... A61B 2017/00367; A61B 2017/00389; A61B 2017/00305; A61B 2017/00309; A61B 2017/00331; A61B 2017/00353; A61B 2017/320032; A61B 2017/3433; A61B 5/150511
See application file for complete search history.

(56) References Cited

U.S. PATENT DOCUMENTS

| | | |
|---|---|---|
| 2,162,681 A | 6/1939 | Ryan |
| 3,473,170 A | 10/1969 | Haase et al. |
| 3,638,643 A | 2/1972 | Hotchkiss |
| 3,741,197 A | 6/1973 | Sanz et al. |
| 3,807,404 A | 4/1974 | Weissman et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,406,282 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,712,537 A | 12/1987 | Pender |
| 4,750,491 A * | 6/1988 | Kaufman ................ A61F 9/013 606/166 |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,861 A | 4/1992 | Narboni |
| 5,135,478 A | 8/1992 | Sibalis |
| 5,158,540 A | 10/1992 | Wijay |
| 5,178,623 A | 1/1993 | Cinberg et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson et al. |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A | 7/1998 | Money |
| 5,792,100 A | 8/1998 | Shantha |
| 5,827,295 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A | 2/2000 | Hill |
| 6,039,748 A | 3/2000 | Savage et al. |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,077,179 A | 6/2000 | Liechty, II |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,251,121 B1 | 6/2001 | Saadat |
| 6,258,067 B1 | 7/2001 | Hill |
| D450,843 S | 11/2001 | McGuckin, Jr. et al. |
| 6,358,231 B1 | 3/2002 | Schindler et al. |
| 6,398,758 B1 | 6/2002 | Jacobsen et al. |
| 6,416,512 B1 | 7/2002 | Ellman et al. |
| 6,440,102 B1 | 8/2002 | Arenberg et al. |
| 6,447,522 B2 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,253 B1 | 4/2003 | Chang |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 | 10/2012 | Tekulve |
| 8,409,175 B2 | 4/2013 | Lee et al. |
| 8,425,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,320,652 B2 | 4/2016 | Andreas et al. |
| 9,387,124 B2 | 7/2016 | Clifford |
| 9,539,146 B2 | 1/2017 | Girotra et al. |
| 2001/0020173 A1 | 9/2001 | Klumb et al. |

(56) References Cited

U.S. PATENT DOCUMENTS

| | | |
|---|---|---|
| 2002/0026125 A1 | 2/2002 | Leysieffer |
| 2002/0069883 A1 | 6/2002 | Hirchenbain |
| 2002/0111585 A1 | 8/2002 | Lafontaine |
| 2002/0138091 A1 | 9/2002 | Pflueger |
| 2002/0161379 A1 | 10/2002 | Kaplan et al. |
| 2002/0169456 A1 | 11/2002 | Tu et al. |
| 2003/0018291 A1 | 1/2003 | Hill et al. |
| 2003/0040717 A1 | 2/2003 | Saulenas et al. |
| 2003/0060799 A1 | 3/2003 | Arenberg et al. |
| 2003/0187456 A1 | 10/2003 | Perry |
| 2003/0199791 A1 | 10/2003 | Boecker et al. |
| 2004/0054339 A1 | 3/2004 | Ciok et al. |
| 2004/0064024 A1 | 4/2004 | Sommer |
| 2005/0033343 A1 | 2/2005 | Chermoni |
| 2005/0165368 A1 | 7/2005 | Py et al. |
| 2005/0182385 A1 | 8/2005 | Epley |
| 2005/0187546 A1 | 8/2005 | Bek et al. |
| 2005/0235422 A1 | 10/2005 | Wallace |
| 2005/0240147 A1 | 10/2005 | Makower et al. |
| 2006/0004323 A1 | 1/2006 | Chang et al. |
| 2006/0095050 A1 | 5/2006 | Hartley et al. |
| 2006/0142700 A1 | 6/2006 | Sobelman et al. |
| 2006/0155304 A1 | 7/2006 | Kaplan et al. |
| 2006/0161218 A1 | 7/2006 | Danilov |
| 2006/0163313 A1 | 7/2006 | Larson |
| 2006/0282062 A1 | 12/2006 | Ishikawa et al. |
| 2007/0233222 A1 | 10/2007 | Roeder et al. |
| 2007/0276466 A1 | 11/2007 | Lavelle et al. |
| 2008/0027423 A1 | 1/2008 | Choi et al. |
| 2008/0051804 A1 | 2/2008 | Cottler et al. |
| 2008/0065011 A1 | 3/2008 | Marchand et al. |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163828 A1 | 6/2009 | Turner et al. |
| 2009/0209972 A1 | 8/2009 | Loushin et al. |
| 2009/0299344 A1 | 12/2009 | Lee et al. |
| 2009/0299379 A1 | 12/2009 | Katz et al. |
| 2009/0299433 A1 | 12/2009 | Dingman et al. |
| 2010/0041447 A1 | 2/2010 | Graylin |
| 2010/0048973 A1 | 2/2010 | Decoodt et al. |
| 2010/0061581 A1 | 3/2010 | Soetejo et al. |
| 2010/0198135 A1 | 8/2010 | Morriss et al. |
| 2010/0217296 A1 | 8/2010 | Morriss et al. |
| 2010/0274188 A1 | 10/2010 | Chang et al. |
| 2010/0324488 A1* | 12/2010 | Smith ............... A61B 17/3417 604/164.11 |
| 2011/0015645 A1* | 1/2011 | Liu .................... A61B 17/3468 606/109 |
| 2011/0022069 A1 | 1/2011 | Mitusina |
| 2011/0077579 A1 | 3/2011 | Harrison et al. |
| 2011/0288559 A1 | 11/2011 | Shahoian |
| 2012/0179187 A1 | 7/2012 | Loushin et al. |
| 2012/0265097 A1 | 10/2012 | Melchiorri et al. |
| 2012/0310145 A1 | 12/2012 | Clifford et al. |
| 2013/0030456 A1* | 1/2013 | Assell ................ A61B 17/1617 606/170 |
| 2013/0090544 A1 | 4/2013 | Clifford et al. |
| 2013/0338678 A1 | 12/2013 | Loushin et al. |
| 2014/0094733 A1 | 4/2014 | Clopp et al. |
| 2014/0100584 A1 | 4/2014 | Konstorum et al. |
| 2014/0194891 A1 | 7/2014 | Shahoian |
| 2014/0276906 A1 | 9/2014 | Andreas et al. |
| 2014/0277050 A1 | 9/2014 | Andreas et al. |
| 2015/0142029 A1* | 5/2015 | Fahn .................... A61F 11/006 606/162 |
| 2015/0164695 A1 | 6/2015 | Liu et al. |
| 2015/0209509 A1* | 7/2015 | O'Cearbhaill ..... A61B 17/3401 604/506 |
| 2015/0305944 A1 | 10/2015 | Kaplan et al. |
| 2016/0038341 A1 | 2/2016 | Clopp et al. |
| 2016/0038342 A1 | 2/2016 | Van et al. |
| 2016/0045370 A1 | 2/2016 | Andreas et al. |
| 2016/0045371 A1 | 2/2016 | Girotra et al. |
| 2016/0213519 A1 | 7/2016 | Andreas et al. |

FOREIGN PATENT DOCUMENTS

| | | |
|---|---|---|
| DE | 19918288 A1 | 10/2000 |
| EP | 0214527 A1 | 3/1987 |
| FR | 2526656 | 11/1983 |
| JP | H 07-116190 A | 5/1995 |
| WO | WO 99/11175 A1 | 3/1999 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2011/008948 | 1/2011 |
| WO | WO 2014/075949 | 5/2014 |
| WO | WO 2014/143543 | 9/2014 |
| WO | WO 2014/158571 | 10/2014 |
| WO | WO 2016/022899 | 2/2016 |
| WO | WO 2016/025308 | 2/2016 |
| WO | WO 2016/025309 | 2/2016 |
| WO | WO 2016/025310 | 2/2016 |
| WO | WO 2016/025453 | 2/2016 |

OTHER PUBLICATIONS

Patent Examination Report No. 1 for Australian Patent Application No. 2013209354, dated Oct. 13, 2014, 5 pages.
First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Office Action for European Application No. 08746237.0, dated Mar. 24, 2016, 3 pages.
Office Action for European Application No. 08746237.0, dated Aug. 4, 2015, 7 pages.
Supplementary Partial Search Report for European Application No. 08746237.0, dated Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
International Search Report for International Application No. PCT/US2008/060779, dated Sep. 3, 2008.
Written Opinion for International Application No. PCT/US2008/060779, dated Sep. 3, 2008.
International Preliminary Report on Patentability for International Application No. PCT/US2008/060779, dated Nov. 17, 2009.
Office Action for U.S. Appl. No. 11/749,729, dated May 26, 2011, 11 pages.
Office Action for U.S. Appl. No. 11/749,729, dated Jun. 17, 2010, 8 pages.
Office Action for U.S. Appl. No. 11/749,733, dated Jun. 10, 2009, 13 pages.
Office Action for U.S. Appl. No. 11/749,733, dated Dec. 2, 2008, 9 pages.
U.S. Appl. No. 61/085,360, filed Jul. 31, 2008.
International Search Report for International Application No. PCT/US2009/052395, dated Nov. 6, 2009.
Written Opinion for International Application No. PCT/US2009/052395, dated Nov. 6, 2009.
International Search Report for International Application No. PCT/US2010/058718, dated Feb. 17, 2011.
Written Opinion for International Application No. PCT/US2010/058718, dated Feb. 17, 2011.
U.S. Appl. No. 61/225,893, filed Jul. 15, 2009.
Patent Examination Report No. 1 for Australian Application No. 2010273372, dated Nov. 12, 2014, 2 pages.

(56) References Cited

OTHER PUBLICATIONS

Office Action for Canadian Application No. 2,768,009, dated Aug. 4, 2016, 4 pages.
First Office Action for Chinese Application No. 201080041755.6, dated Jul. 3, 2013.
Notification of Reasons for Refusal for Japanese Application No. 2012-520778, dated Feb. 18, 2014.
Communication of the Substantive Examination Report for Mexican Application No. MX/a/2012/000691, dated Apr. 24, 2014.
International Search Report for International Application No. PCT/US2010/042128, dated Aug. 27, 2010.
Written Opinion International Application No. PCT/US2010/042128, dated Aug. 27, 2010.
International Preliminary Report on Patentability for International Application No. PCT/US2010/042128, dated Jan. 17, 2012.
European Search Report for European Application No. 13173409.7, dated Sep. 16, 2013.
Search Report and Written Opinion for International Patent Application No. PCT/US2015/044179, dated Dec. 18, 2015, 15 pages.
International Search Report and Written Opinion for International Application No. PCT/US2014/018320, dated Jun. 2, 2014, 10 pages.
International Search Report and Written Opinion for International Application No. PCT/US2014/018347, dated Apr. 17, 2014, 9 pages.
International Search Report and Written Opinion for International Application No. PCT/US2015/044173, dated Oct. 12, 2015, 9 pages.
International Search Report and Written Opinion for International Application No. PCT/US2015/044177, dated Oct. 30, 2015, 10 pages.
International Search Report and Written Opinion for International Application No. PCT/US2015/044610, dated Nov. 5, 2015, 12 pages.
International Search Report for International Application No. PCT/US2009/069388, dated Jun. 30, 2010.
Written Opinion for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.
Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).
Lindeman et al., the "Arrow Tube" Residents in Otolaryngology, Massachusetts Eye and Ear Infirmary, 1 page (1964).
Pappas, "Middle Ear Ventilation Tubes" Meeting of the Southern Section of the American Laryngological, Rhinological and Otological Society, Inc., Williamsburg, VA, Jan. 12, 1974, pp. 1098-1117.
Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.
Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.
Ringenberg, "A New Middle Ear Ventilation Device" Seventy-second Annual Session of the American Academy of Ophthalmology and Otolaryngology, Oct. 29-Nov. 3, 1967, Chicago, IL, 1 page.
Schmidt et al. "Transtympanic Aeration of the Middle Ear With Blocked Eustachian Tube" Acta Otolaryng., pp. 277-282 (1965).
Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.
Santa Barbara Medco, Inc. "Otological Ventilation Tubes" Product Brochure from http://www.sbmedco.com/ptfe_shepard.asp, 8 pages (Feb. 11, 2001).
Rhinology Products, Boston Medical Products, www.bosmed.com [date of publication unknown], pp. 1-16.

* cited by examiner

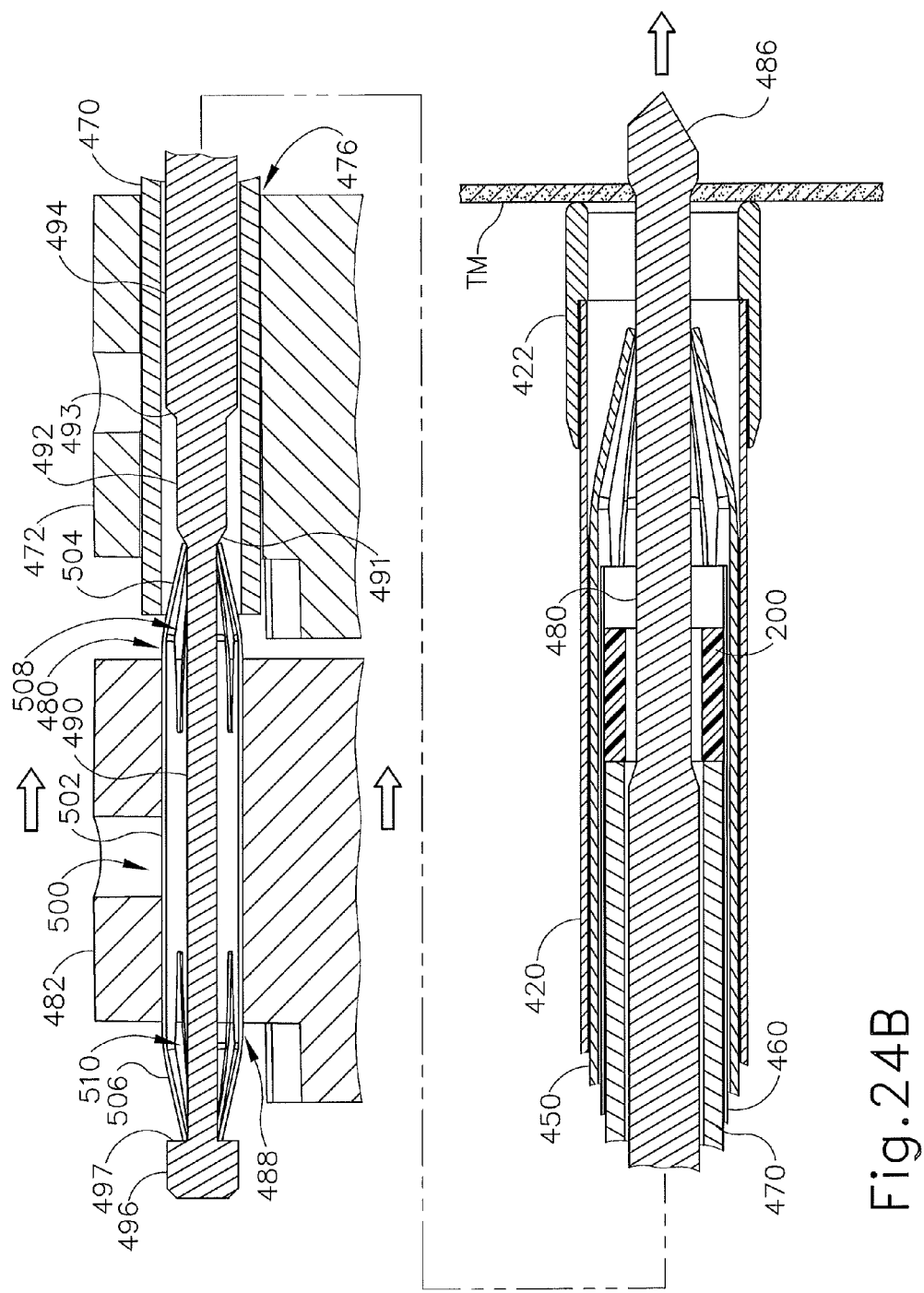

US 9,833,359 B2

TYMPANOSTOMY TUBE DELIVERY DEVICE WITH CUTTER FORCE CLUTCH

BACKGROUND

Some children may exhibit recurrent episodes of otitis media and/or otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012; and U.S. Pub. No. 2011/0015645, entitled "Tympanic Membrane Pressure Equalization Tube Delivery System," published Jan. 20, 2011, the disclosure of which is incorporated by reference herein. Still additional exemplary pressure equalization tube delivery systems are disclosed in U.S. patent application Ser. No. 13/804,553, entitled "Features to Improve and Sense Tympanic Membrane Apposition by Tympanostomy Tube Delivery Instrument," filed Mar. 14, 2013, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 24B depicts a cross-sectional side elevational view of the shaft assembly of FIG. 16, with the follower of FIG. 24A, the piercer of FIG. 19, and the clutch of FIG. 19 moved distally to a second longitudinal position so as to pierce a tympanic membrane;

Figure 1:
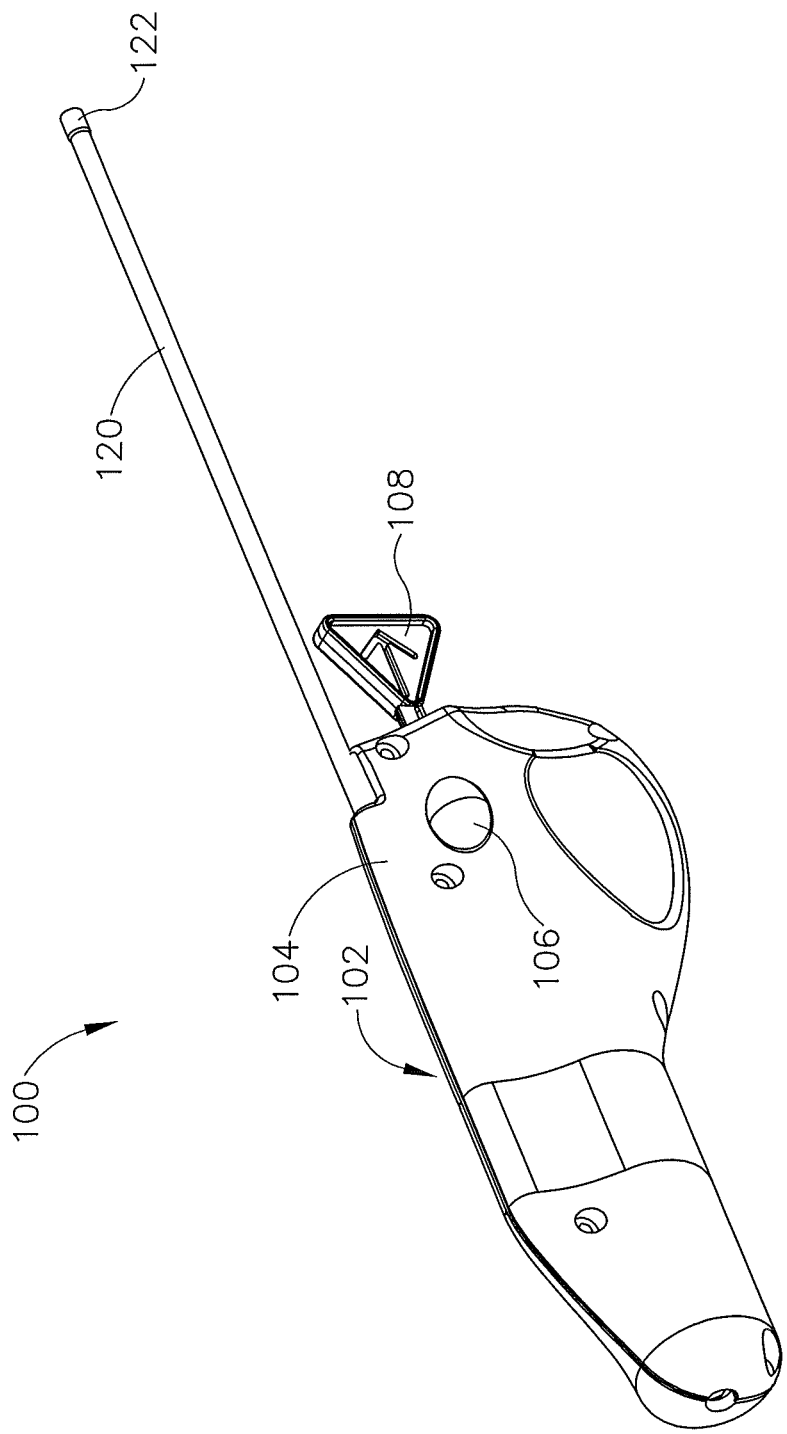
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Pressure Equalization Tube Delivery Instrument

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary equalization tube delivery device (PETDD) (100) that may be used in such procedures. It should be understood that PETDD (100) may be used with an endoscope to provide visualization of the tympanic membrane (TM) during use of PETDD (100). It should also be understood that a patient may receive local anesthesia at the tympanic membrane (TM) through a process of iontophoresis before PETDD (100) is actuated to deploy a PE tube. By way of example only, such iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. Other suitable ways in which PETDD (100) may be used will be apparent to those of ordinary skill in the art in view of the teachings herein.

As shown in FIG. 1, PETDD (100) of this example comprises a handpiece (102) and a cannula (120) extending distally from handpiece (102). Hanpdiece (102) is formed by two housing (104) halves that are joined together and that include internal features configured to support various components of PETDD (100) as will be described below. Handpiece (102) is configured to be handheld, such that an operator may fully operate PETDD (100) using a single hand. A pushbutton (106) is slidably disposed in housing (104) and includes exposed portions extending laterally from each side of handpiece. Pushbutton (106) is operable to be pushed along a path that is transverse to handpiece (102) in order to actuate PETDD (100) as will be described in greater detail below. A pull-pin (108) extends distally from handpiece (102) and is configured to prevent pushbutton (106) from being actuated, thereby preventing PETDD (100) from being actuated, so long as pull-pin (108) is disposed in handpiece (102). Pull-pin (108) is nevertheless removable from handpiece (102) to effectively unlock pushbutton (106) and thereby enable actuation of PETDD (100). Cannula (120) of the present example comprises an elongate tube having a clear tip member (122) at the distal end of cannula (120). Clear tip member (122) is configured to contact a patient's tympanic membrane (TM) while enabling visualization of the distal end of cannula (120). In some versions, tip member (122) is formed of a soft or elastomeric material such as rubber, soft plastic, etc. This may dampen vibrations that might otherwise be transmitted from cannula (120) to the patient's tympanic membrane (TM) during firing of PETDD (100). In addition or in the alternative, tip member (122) may include some other kind of dampening feature as will be apparent to those of ordinary skill in the art in view of the teachings herein.

Figure 2:
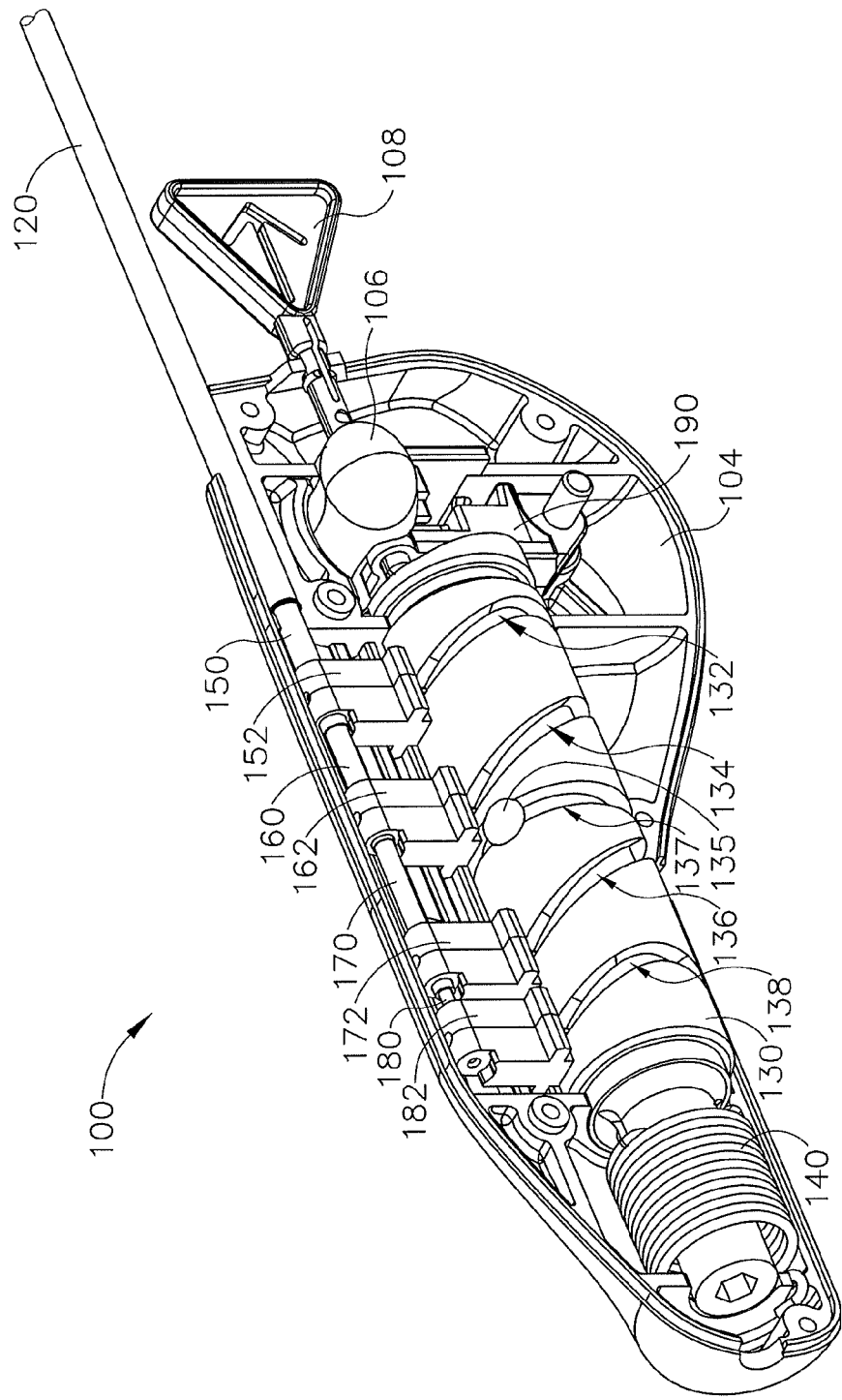
FIG. 2 depicts a perspective view of the PETDD of FIG. 1, with a housing half omitted.

As can be seen in FIG. 2, housing (104) supports a camshaft (130) and various other components. Camshaft (130) includes a dilator track (132), a shield tube track (134), a stopper track (137), a pusher track (136), and a piercer track (138). Tracks (132, 134, 136, 137, 138) are formed as recesses in camshaft (130) and each track (132, 134, 136, 137, 138) has a unique configuration in order to provide a particular sequence of operation of translating components as will be described in greater detail below. A torsion spring (140) is coupled to the proximal end of camshaft (130). Torsion spring (140) is also grounded against housing (104). Torsion spring (140) resiliently provides a rotational bias to camshaft (130). In particular, torsion spring (140) urges camshaft (130) to rotate in the clockwise direction (viewed from the distal end of PETDD (100) toward the proximal end of PETDD (100)) about the longitudinal axis of camshaft (130). As will be described in greater detail below (200), a trigger mechanism selectively resists such rotation. While torsion spring (140) is used to bias camshaft (130) in the present example, it should be understood that any other suitable types of components may be used to bias camshaft (130).

Figure 3:
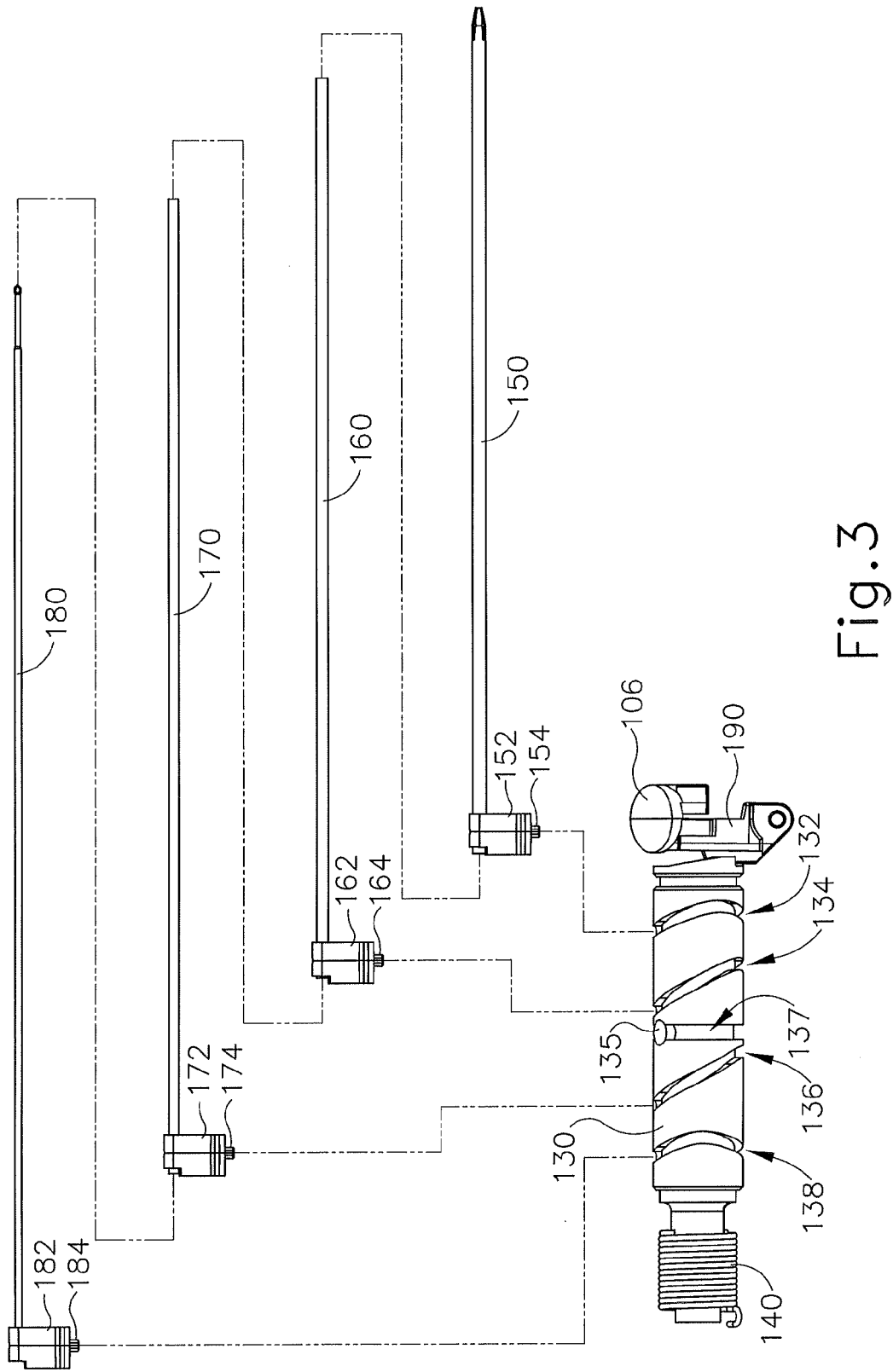
FIG. 3 depicts an exploded elevational view of actuation features of the PETDD of FIG. 1.

As shown in FIG. 3, various components are engaged with camshaft (130) and are thereby actuated by rotation of camshaft (130). In particular, a dilator tube (150), a shield tube (160), a pusher tube (170), and a piercer (180) are all engaged with camshaft (130). Tubes (150, 160, 170) and piercer (180) are all coaxially disposed within cannula (120). Piercer (180) is coaxially and slidably disposed within pusher tube (170), which is coaxially and slidably disposed within shield tube (160), which is coaxially and slidably disposed within dilator tube (150), which is coaxially and slidably disposed within cannula (120). Tubes (150, 160, 170) and piercer (180) all translate relative to cannula (120) in a particular sequence in order to deploy a PE tube as will be described in greater detail below. This sequence is driven by rotation of camshaft (130).

A cam follower (152) is fixedly secured to the proximal end of dilator tube (150). Cam follower (152) includes a laterally projecting pin (154) that is disposed in dilator track (132), such that rotation of camshaft (130) causes cam follower (152) and dilator tube (150) to translate. Similarly, a cam follower (162) is fixedly secured to the proximal end of shield tube (160). Cam follower (162) includes a laterally projecting pin (164) that is disposed in shield tube track (134), such that rotation of camshaft (130) causes cam follower (162) and shield tube (160) to translate. A cam follower (172) is fixedly secured to the proximal end of pusher tube (170). Cam follower (172) includes a laterally projecting pin (174) that is disposed in pusher tube track (136), such that rotation of camshaft (130) causes cam follower (172) and pusher tube (170) to translate. Finally, a cam follower (182) is fixedly secured to the proximal end of piercer (180). Cam follower (182) includes a laterally projecting pin (184) that is disposed in piercer track (138), such that rotation of camshaft (130) causes cam follower (182) and piercer (180) to translate. Stopper track (137) is simply annular in this example and includes a fixed elastomeric plug (135). An inwardly protruding boss (not shown) of housing (104) is disposed in stopper track (137). This boss remains disposed in stopper track (137) during rotation of camshaft (130).

Figure 4:
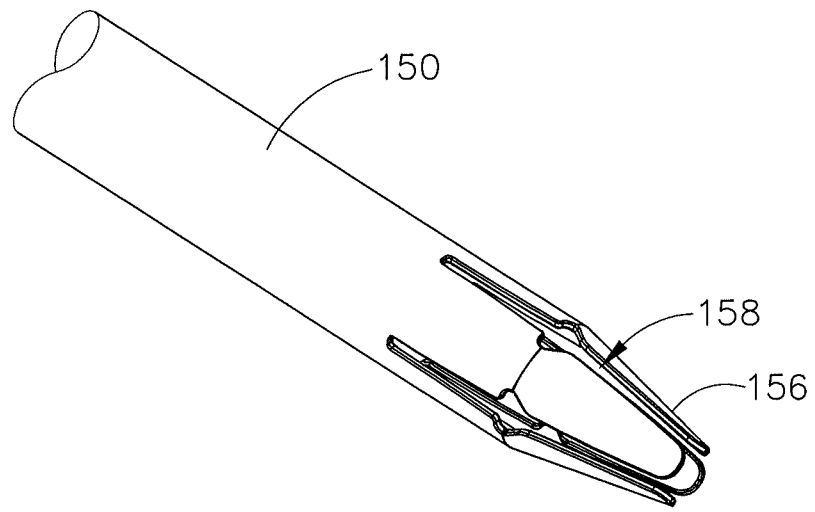
FIG. 4 depicts a perspective view of the distal end of a dilator of the actuation features of FIG. 3.
Figure 5:
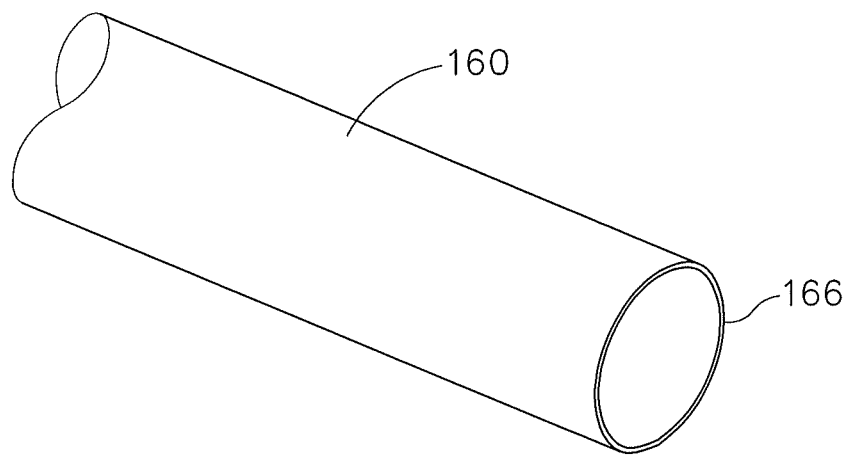
FIG. 5 depicts a perspective view of the distal end of a shield tube of the actuation features of FIG. 3.
Figure 6:
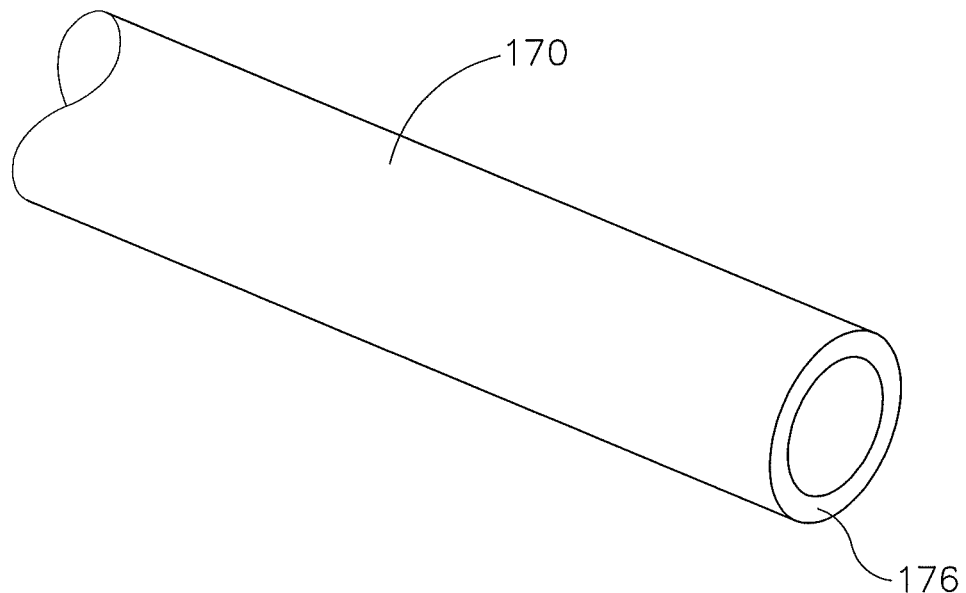
FIG. 6 depicts a perspective view of the distal end of a pusher of the actuation features of FIG. 3.
Figure 7:
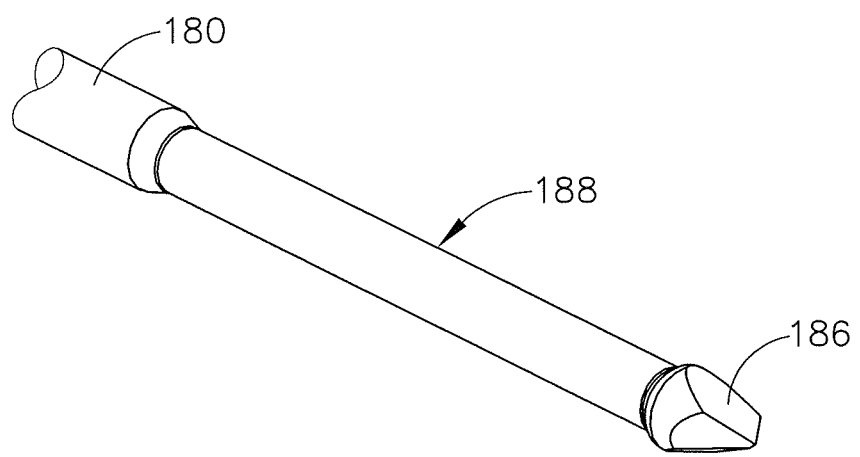
FIG. 7 depicts a perspective view of the distal end of a piercer of the actuation features of FIG. 3.

As shown in FIG. 4, the distal end of dilator tube (150) includes a plurality of generally flexible leaves (156) that are separated by longitudinally extending gaps (158). Leaves (156) are resiliently biased to assume the inwardly deflected positioning shown in FIG. 4; but are operable to flex outwardly from this positioning as will be described in greater detail below. As shown in FIG. 5, the distal end of shield tube (160) simply includes a circular edge (166). As shown in FIG. 6, the distal end of pusher tube (170) includes a distal face (176). In the present example, the difference between the inner diameter of pusher tube (170) and the outer diameter of pusher tube (170) is greater than the difference between the inner diameter of shield tube (160) and the outer diameter of shield tube (160). Thus, distal face (176) presents a more prominent contact surface than circular edge (166). As shown in FIG. 7, the distal end of piercer (180) includes a sharp, multi-faceted piercer tip (186) that is configured to pierce through a patient's tympanic membrane (TM). In the present example, piercer (180) also includes a neck-down region (188) having a reduced diameter.

Figure 8:
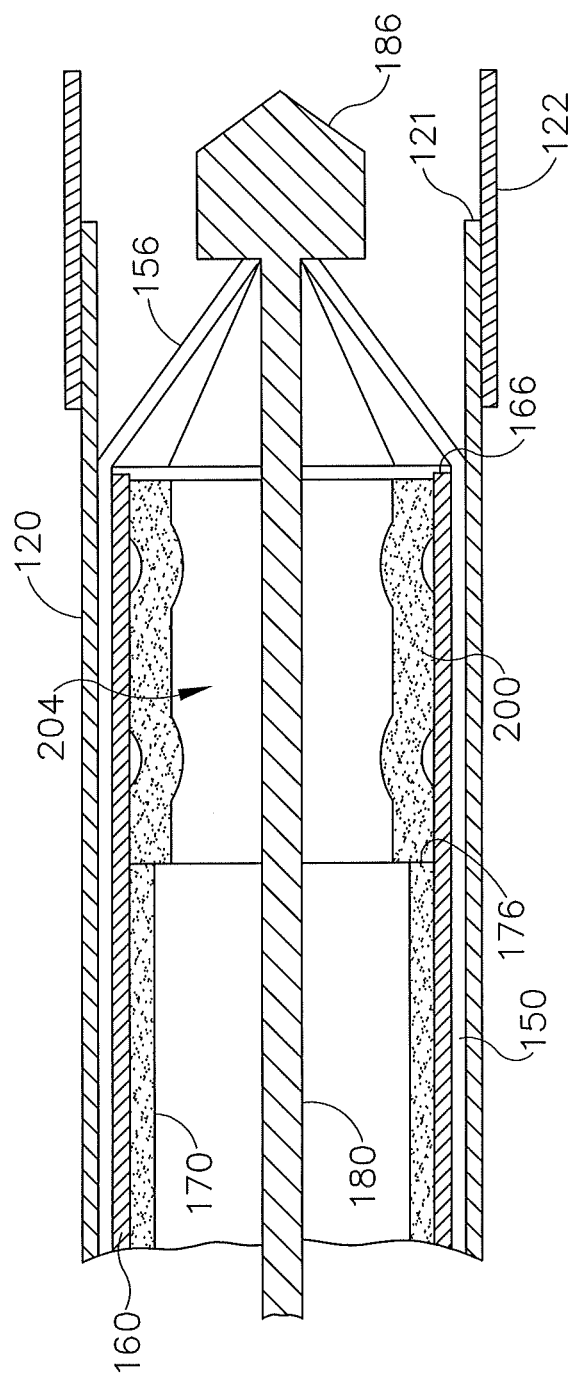
FIG. 8 depicts a cross-sectional side view of the actuation features of FIG. 3 with an exemplary pressure equalization (PE) tube.

FIG. 8 shows the positioning of tubes (150, 160, 170), piercer (180), and PE tube (200) within cannula (120) before camshaft (130) starts rotating from a home position. As shown, piercer tip (186) of piercer (180) is positioned distal to leaves (156) of dilator tube (150), such that leaves (156) are positioned about neck-down region (188) of piercer (180). PE tube (200) is positioned within the distal end of shield tube (160), whose distal edge (166) is just proximal to leaves (156). Pusher tube (170) is proximal to PE tube (200), with distal face (176) of pusher tube (170) abutting the proximal end of PE tube (200). In the present example, PE tube (200) is resiliently biased to assume a rivet-like shape presenting transverse petals (208) and a flange (206) (see FIG. 9). However, PE tube (200) is compressed against this bias, thereby assuming a generally cylindraceous configuration, when PE tube (200) is disposed within shield tube (160) as shown in FIG. 8.

Figure 9:
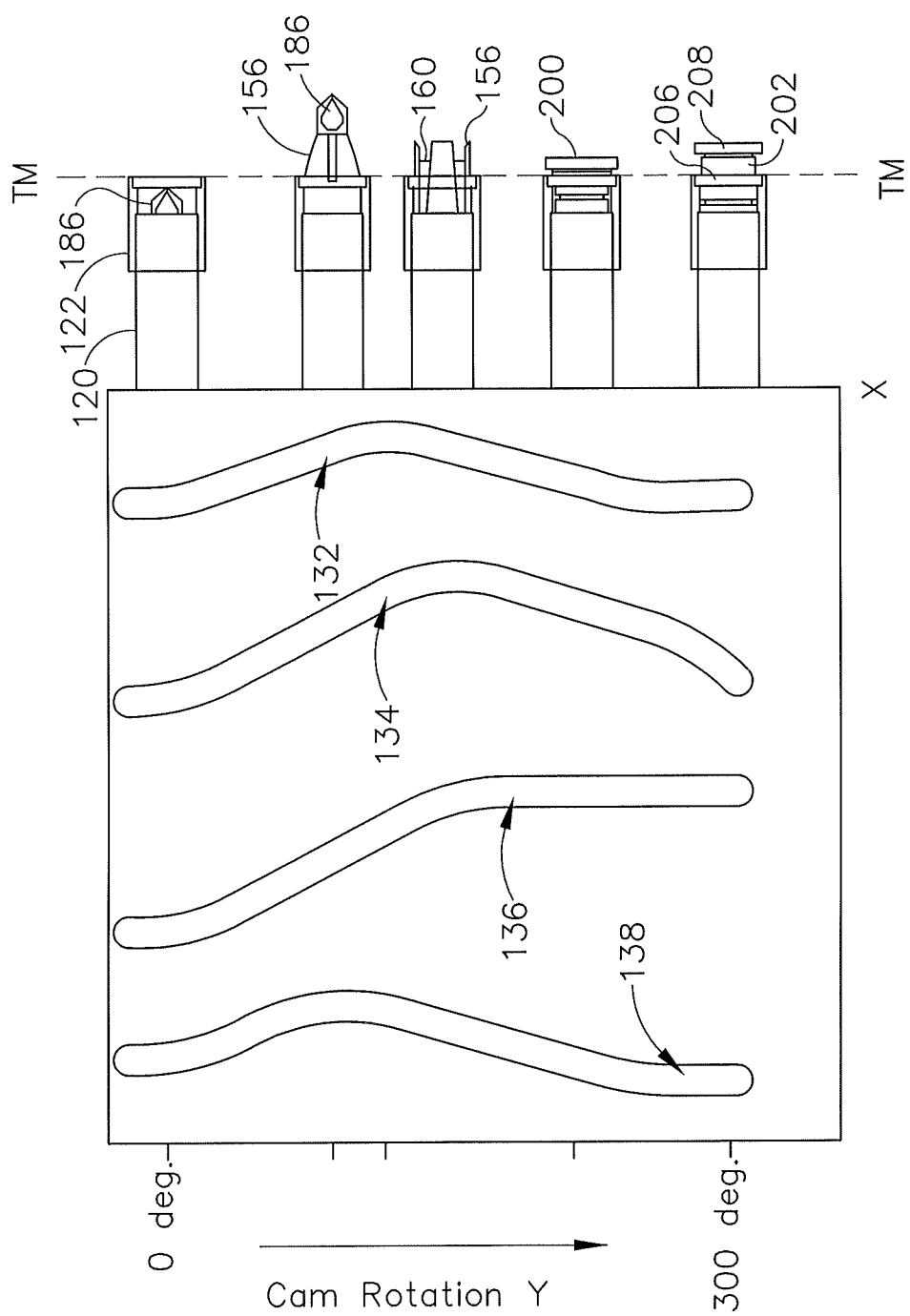
FIG. 9 depicts a displacement and operational diagram associated with the actuation features of FIG. 3.
Figure 10:
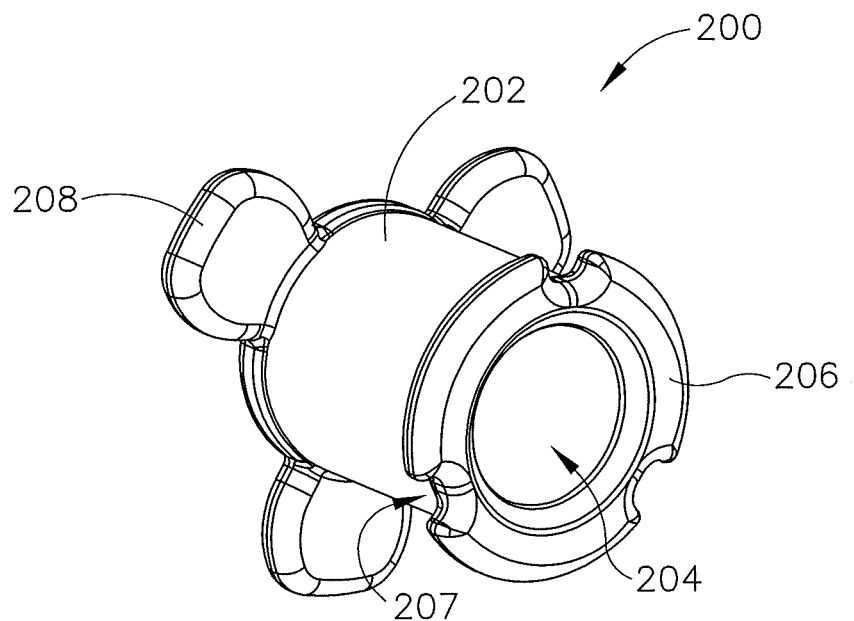
FIG. 10 depicts a perspective view of the proximal side of an exemplary PE tube suitable for delivery by the PETDD of FIG. 1.
Figure 11:
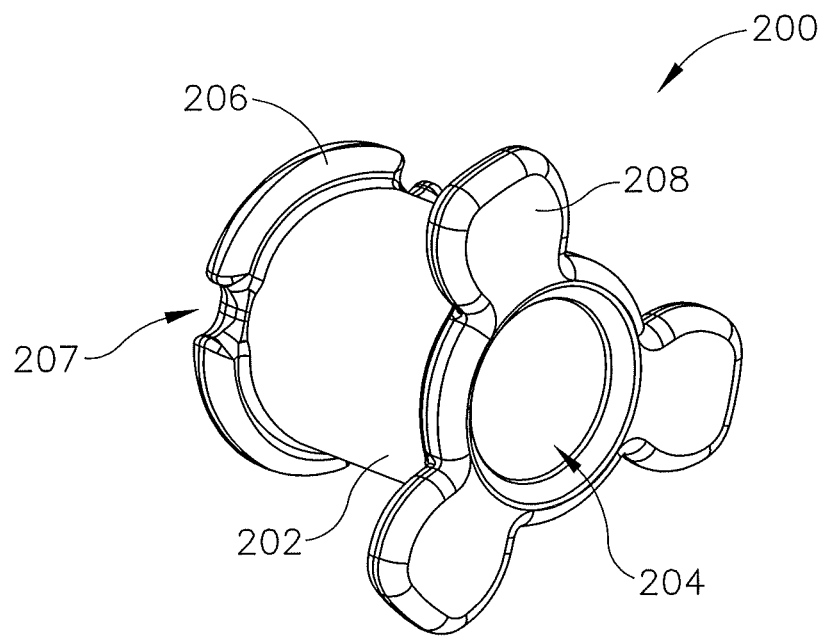
FIG. 11 depicts a perspective view of the distal side of the PE tube of FIG. 10.
Figure 12:
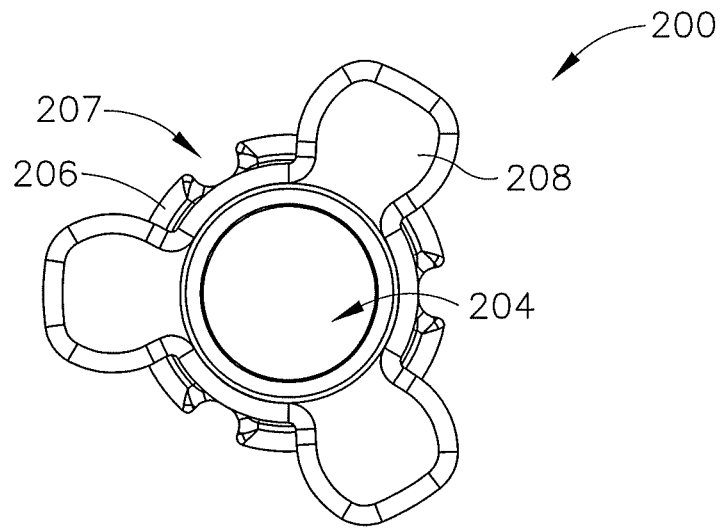
FIG. 12 depicts a distal elevational view of the PE tube of FIG. 10.
Figure 13:
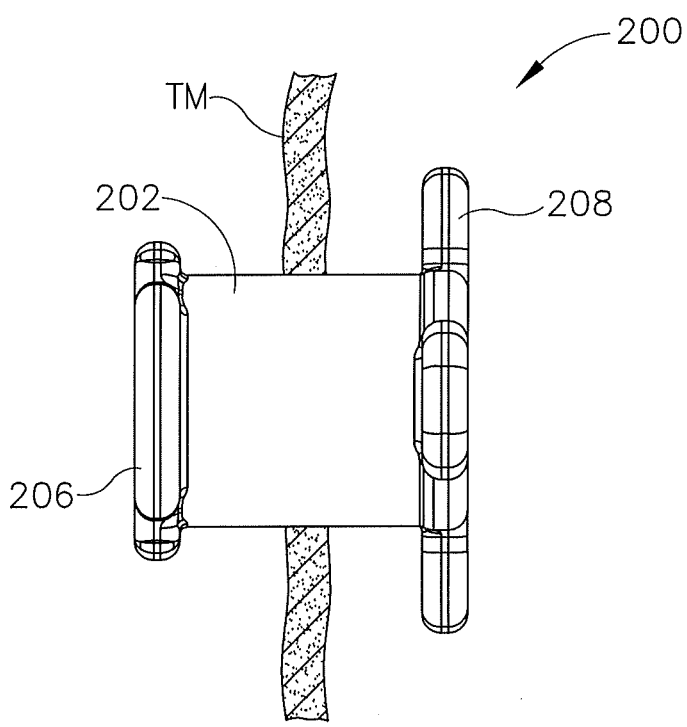
FIG. 13 depicts a side elevational view of the PE tube of FIG. 10, positioned within a tympanic membrane.

FIG. 9 depicts a sequence of operation that occurs upon rotation of camshaft (130) from a home position to an actuated position, where tracks (132, 134, 136, 138) are shown developed into a flat pattern for purpose of illustration. The sequence starts at the top region of FIG. 9, which shows the distal end of clear tip member (122) contacting the patient's tympanic membrane (TM). At this stage, tubes (150, 160, 170), piercer (180), and PE tube (200) are at the positions shown in FIG. 8. Once camshaft (130) starts rotating at the urging of torsion spring (140), pins (154, 164, 174, 184) begin to ride along their respective tracks (132, 134, 136, 138), such that piercer tip (186) and leaves (156) are driven distally through the patient's tympanic membrane (TM). While not directly shown in FIG. 8, it should be understood that tubes (160, 170, 190) are also driven distally during this transition, though tubes (160, 170, 190) remain proximal to clear tip member (122) at this stage. As camshaft (130) continues to rotate, piercer (180) begins retracting proximally while tubes (160, 170, 190) continue to advance distally. As shown, shield tube (160) spreads leaves (156) outwardly from their default positions. This further dilates the puncture site in the tympanic membrane (TM). Shield tube (160) continues to contain PE tube (200) at this stage. As camshaft (130) continues to rotate, piercer (180) and dilator (150) retract proximally behind clear tip member (122). Shield tube (160) also begins to retract proximally, while pusher tube (170) remains longitudinally stationary. This relative movement uncovers the distal end of PE tube (200), such that the resilient bias of petals (208) causes petals (208) to flex to transverse positions, thereby effectively forming a flange on the far side of the tympanic membrane (TM). Piercer (180) eventually returns to the fully proximal position, dilator (170) eventually returns to the fully proximal position, and pusher tube (170) eventually reaches a fully distal position. As camshaft (130) continues to rotate, shield tube (160) continues to retract proximally while pusher tube (170) remains longitudinally stationary. This relative movement uncovers the proximal end of PE tube (200), such that the resilient bias of PE tube (200) is allowed to form flange (206) on the near side of the tympanic membrane (TM).

Camshaft (130) stops rotating when the inwardly protruding boss of housing (104) engages plug (135) in stopper track (137). The elastomeric nature of plug (135) provides a relatively soft stop, such that plug (135) acts as a damper. This may reduce jolting of PETDD (100) when camshaft (130) comes to a stop and/or may prevent camshaft (130) from making a popping or snapping sound when camshaft (130) comes to a stop. Upon completion of the above described sequence shown in FIG. 9, cannula (120) is withdrawn from the patient's ear, leaving the actuated PE tube (200) in place in the patient's tympanic membrane (TM). Petals (208) and flange (206) cooperate to maintain the position of PE tube (200) in TM, while the passageway (204) formed by the interior of PE tube (200) (see FIGS. 8 and 10-13) provides a path for fluid communication (e.g., venting) between the patient's middle ear and outer ear. This fluid path further provides pressure equalization between the patient's middle ear and outer ear and/or promotes drainage of fluid from the middle ear via the Eustachian tube.

It should be understood that the foregoing components, features, and operabilities of PETDD (100) are merely illustrative examples. A PETDD (100) may include various other features in addition to or in lieu of those described above. By way of example only, any of the devices herein may also include one or more of the various features disclosed in any of the various references that are incorporated by reference herein. Some additional merely illustrative variations of PETDD (100) will be described in greater detail below, while other variations of PETDD (100) will be apparent to those of ordinary skill in the art in view of the teachings herein.

II. Exemplary Pressure Equalization Tube

FIGS. 10-13 show PE tube (200) in greater detail. PE tube (200) of this example includes a cylindraceous body (202) that defines a passageway (204). A flange (206) is located at the proximal end of body (202) while a set of petals (208) are located at the distal end of body (202). Flange (206) includes a plurality of inwardly directed recesses (207). Recesses (207) are configured to facilitate flexing of flange (206) from an outwardly extended position to a generally cylindraceous position where the material forming flange (206) extends longitudinally. While three recesses (207) are shown, it should be understood that any other suitable number of recesses (207) may be provided. Similarly, while three petals (208) are shown, it should be understood that any other suitable number of petals (208) may be provided.

PE tube (200) is formed of a resilient material that is biased to assume the rivet like configuration shown in FIGS. 10-13. However, flange (206) and petals (208) may be flexed inwardly toward the longitudinal axis of body (202) to provide PE tube (200) with a cylindraceous configuration. In particular, flange (206) and petals (208) may be flexed such that their outer surfaces are at the same radial distance from the longitudinal axis as the outer perimeter of body (202). This radial distance may be slightly less than the radial distance associated with the inner diameter of shield tube (160), such that PE tube (200) may collapse to fit within shield tube (160). When PE tube (200) is disposed in a tympanic membrane (TM), petals (208) are located medially (i.e., on the middle ear side) while flange (206) is located laterally (i.e., on the outer ear side). By way of example only, PE tube (200) may also be configured in accordance with at least some of the teachings of U.S. patent application Ser. No. 13/800,113, entitled "Tympanic Membrane Pressure Equalization Tube," filed on Mar. 13, 2013, the disclosure of which is incorporated by reference herein. Other suitable forms that PE tube (200) may take will be apparent to those of ordinary skill in the art in view of the teachings herein.

III. Exemplary Pressure Equalization Tube Delivery with Force Limiting Piercer

It will be appreciated that a piercer (180) of a PETDD (100) may mistakenly or inadvertently come into contact with a surface not intended to be pierced. Such mistaken or inadvertent contact may occur during use of the PETDD (100), particularly during actuation of the piercer (180), or may occur during handling or transportation of the PETDD (100). Thus, it may be desirable to provide a PETDD (100) with features configured limit the force applied to or by the piercer (180). Such force limiting features may limit potential injury and/or damage that may be caused by mistaken or inadvertent contact with the piercer (180). For instance, such features may allow for a piercer (180) to penetrate a tympanic membrane but would not allow the piercer to penetrate human skin or bone. As will be discussed in more detail below, FIGS. 14-26E show such an exemplary alternative PETDD (400) having features configured to limit the force applied to or by the piercer. Various examples of such features will be described in greater detail below; while other examples will be apparent to those of ordinary skill in the art according to the teachings herein. It should be understood that PETDD (400) described below is configured to function substantially similar to PETDD (100) described above except for the differences described below. In particular, PETDD (400) described below may be used to insert PE tube (200) within the tympanic membrane (TM) of a patient.

Figure 14:
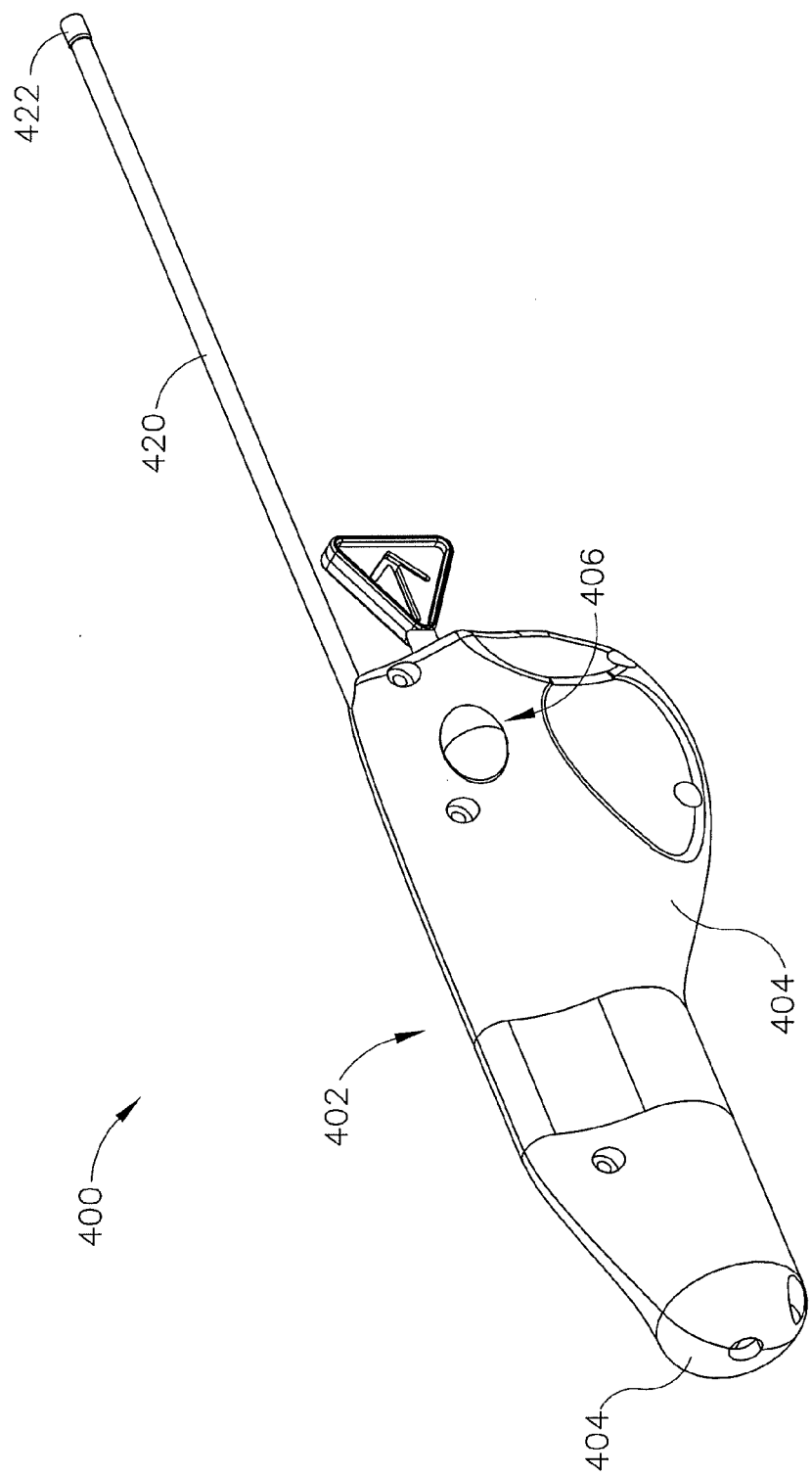
FIG. 14 depicts a perspective view of an exemplary alternative PETDD.

As shown in FIG. 14, PETDD (400) of this example comprises a handpiece (402) and a cannula (420) extending distally from handpiece (402). Hanpdiece (402) is formed by two housing halves (404) that are joined together and that include internal features configured to support various components of PETDD (400). Handpiece (402) is configured to be handheld, such that an operator may fully operate PETDD (400) using a single hand. Cannula (420) of the present example comprises an elongate tube having a clear tip member (422) at the distal end of cannula (420). Tip member (422) is configured to contact a patient's tympanic membrane (TM) while enabling visualization of the distal end of cannula (420). In some versions, tip member (422) is formed of a soft or elastomeric material such as rubber, soft plastic, etc. This may dampen vibrations that might otherwise be transmitted from cannula (420) to the patient's tympanic membrane (TM) during firing of PETDD (400). In addition or in the alternative, tip member (422) may include some other kind of dampening feature as will be apparent to those of ordinary skill in the art in view of the teachings herein.

Figure 15:
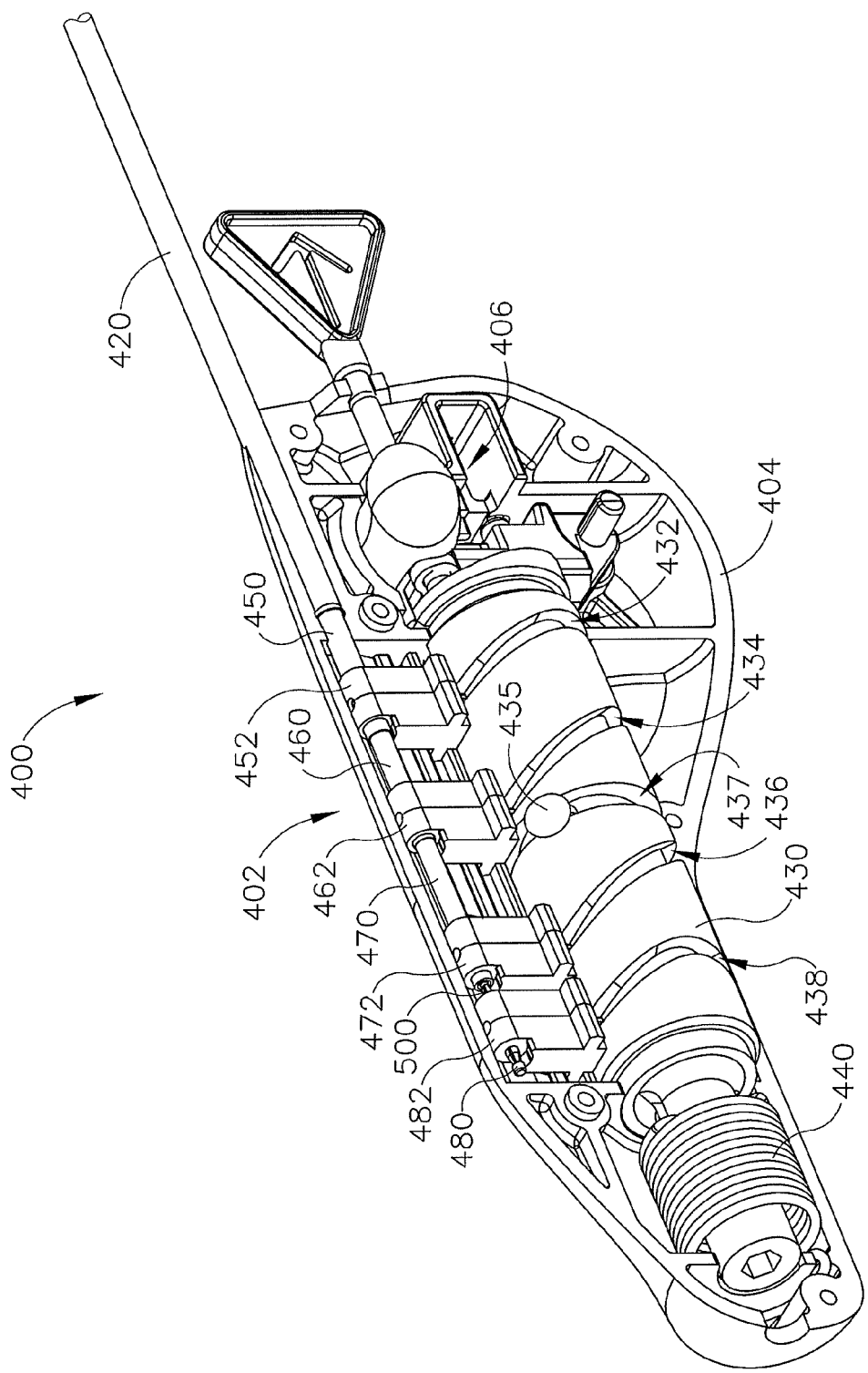
FIG. 15 depicts a perspective view of the PETDD of FIG. 14, with a housing half omitted.
Figure 16:
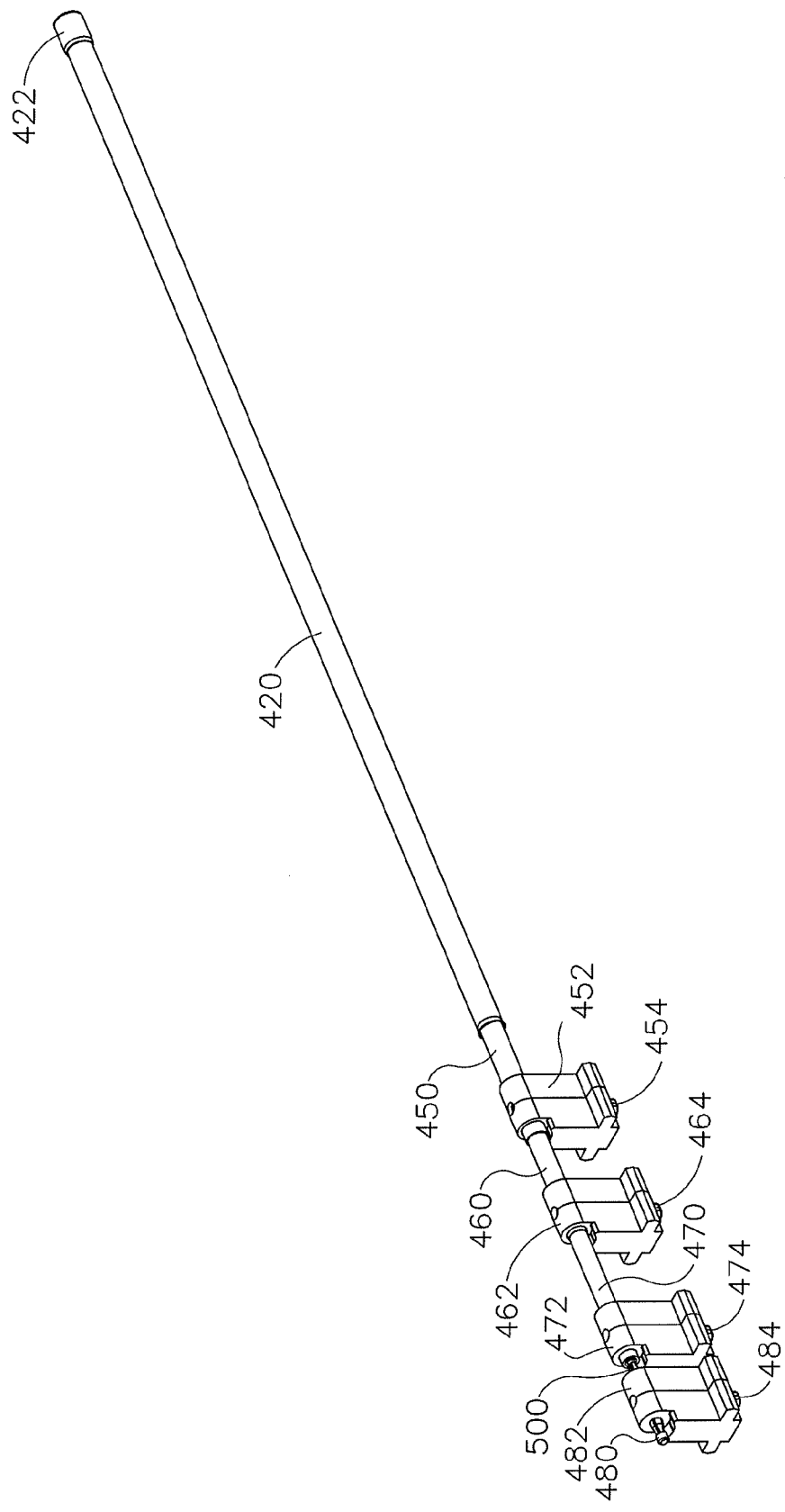
FIG. 16 depicts a perspective view of a shaft assembly of the PETDD of FIG. 14.
Figure 17:
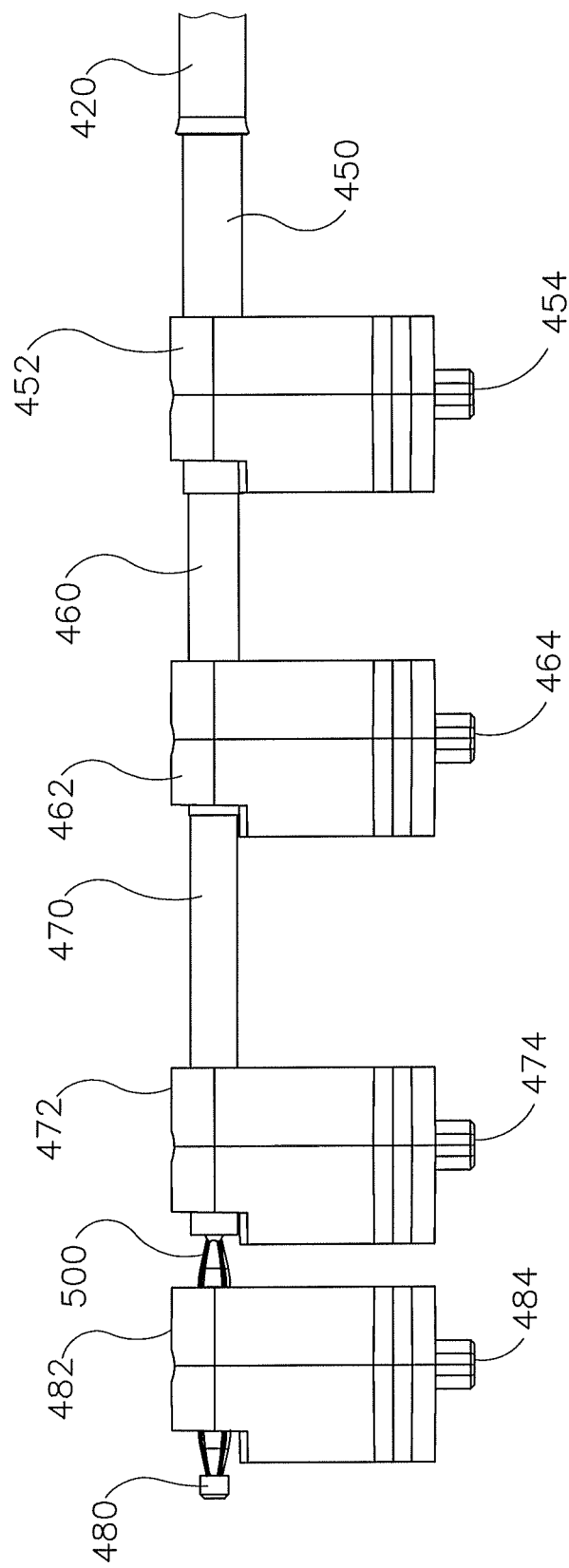
FIG. 17 depicts a side elevational view of a proximal portion of the shaft assembly of FIG. 16.
Figure 18:
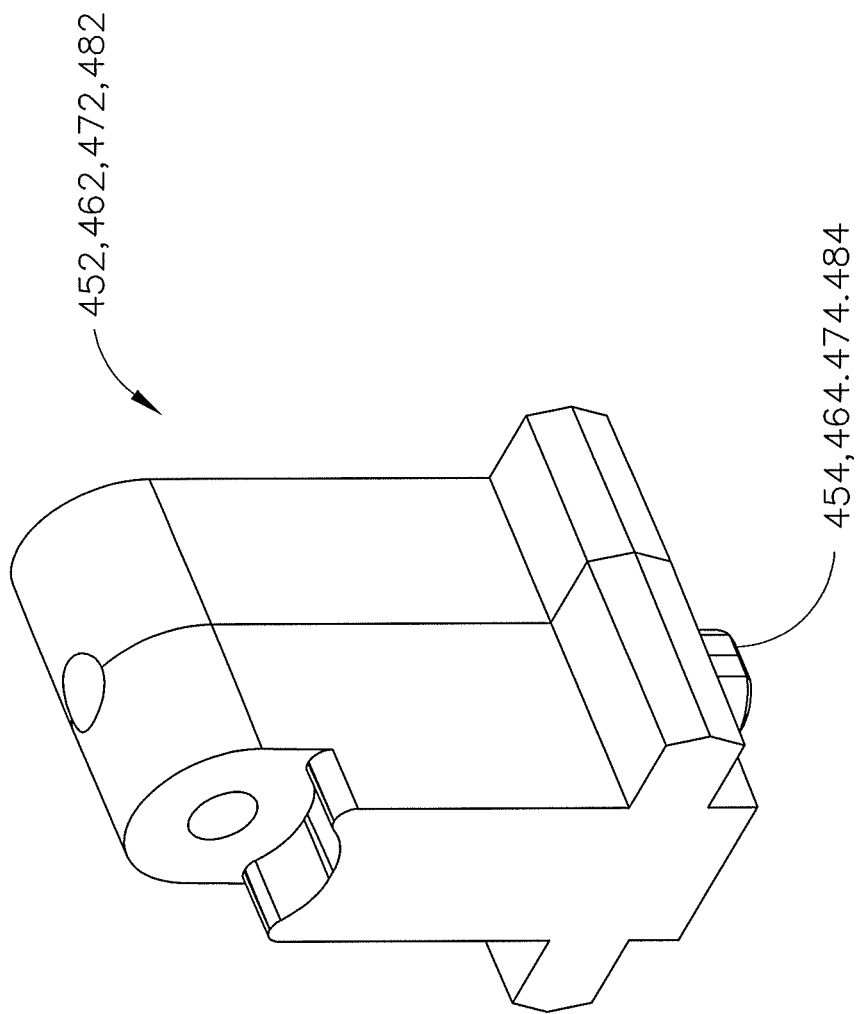
FIG. 18 depicts a perspective view of a follower of the shaft assembly of FIG. 16.

As can be seen in FIG. 15, housing (404) supports a camshaft (430) and various other components. Camshaft (430) is configured to operate substantially similar to camshaft (130). For instance, camshaft (430) is configured to rotate to thereby provide a particular sequence of operation of translating components as described above with reference to PETDD (100). Camshaft (430) includes a dilator track (432), a shield tube track (434), a stopper track (437), a pusher track (436), and a piercer track (438). Tracks (432, 434, 436, 437, 438) are configured to operate substantially similar to tracks (132, 134, 136, 137, 138) discussed above. In particular, tracks (432, 434, 436, 437, 438) are formed as recesses in camshaft (430) and each track (432, 434, 436, 437, 438) has a unique configuration in order to provide a particular sequence of operation of translating components.

A torsion spring (440) is coupled to the proximal end of camshaft (430). Torsion spring (440) is also grounded against housing (404). Torsion spring (440) resiliently provides a rotational bias to camshaft (430). In particular, torsion spring (440) urges camshaft (430) to rotate in the clockwise direction (viewed from the distal end of PETDD (400) toward the proximal end of PETDD (400)) about the longitudinal axis of camshaft (430). A trigger mechanism (406) selectively resists such rotation. By way of example only, trigger mechanism (406) may be configured to operate in accordance with at least some of the teachings of U.S. patent application Ser. No. 13/804,553, entitled "Features to Improve and Sense Tympanic Membrane Apposition by Tympanostomy Tube Delivery Instrument," filed Mar. 14, 2013; and/or U.S. patent application Ser. No. h[ATTORNEY DOCKET NO. ACC5076USNP.0615042], entitled "Trigger Assembly for Tympanostomy Tube Delivery Device," filed on even date herewith, the disclosures of which are incorporated by reference herein. While torsion spring (440) is used to bias camshaft (430) in the present example, it should be understood that any other suitable types of components may be used to bias camshaft (430).

As shown in FIG. 15, various components are engaged with camshaft (430) and are thereby actuated by rotation of camshaft (430). In particular, as best seen in FIG. a dilator tube (450), a shield tube (460), a pusher tube (470), and a piercer (480) are all engaged with camshaft (430). Tubes (450, 460, 470) and piercer (480) are configured to operate substantially similar to tubes (150, 160, 170) and piercer (180) discussed above except for the differences discussed below. Tubes (450, 460, 470) and piercer (480) are all coaxially disposed within cannula (420). Piercer (480) is coaxially and slidably disposed within pusher tube (470), which is coaxially and slidably disposed within shield tube (460), which is coaxially and slidably disposed within dilator tube (450), which is coaxially and slidably disposed within cannula (420). Tubes (450, 460, 470) and piercer (480) all translate relative to cannula (420) in a particular sequence in order to deploy PE tube (200). This sequence is driven by rotation of camshaft (430) as described above with reference to camshaft (130) and PETDD (100).

A cam follower (452) is fixedly secured to the proximal end of dilator tube (450). Cam follower (452) includes a laterally projecting pin (454) that is disposed in dilator track (432), such that rotation of camshaft (430) causes cam follower (452) and dilator tube (450) to translate. Similarly, a cam follower (462) is fixedly secured to the proximal end of shield tube (460). Cam follower (462) includes a laterally projecting pin (464) that is disposed in shield tube track (434), such that rotation of camshaft (430) causes cam follower (462) and shield tube (460) to translate. A cam follower (472) is fixedly secured to the proximal end of pusher tube (470). Cam follower (472) includes a laterally projecting pin (474) that is disposed in pusher tube track (436), such that rotation of camshaft (430) causes cam follower (472) and pusher tube (470) to translate. Finally, a cam follower (482) is selectively slidably coupled to the proximal end of piercer (480) via a clutch (500). In particular, clutch (500) is fixedly secured to cam follower (482), and piercer (480) is indirectly coupled with piercer (480) via clutch (500). As will be discussed in more detail below, clutch (500) is configured to limit the amount of force that may be applied to and/or by piercer (480). Cam follower (482) includes a laterally projecting pin (484) that is disposed in piercer track (438), such that rotation of camshaft (430) causes cam follower (482) and piercer (480) to translate.

Figure 21:
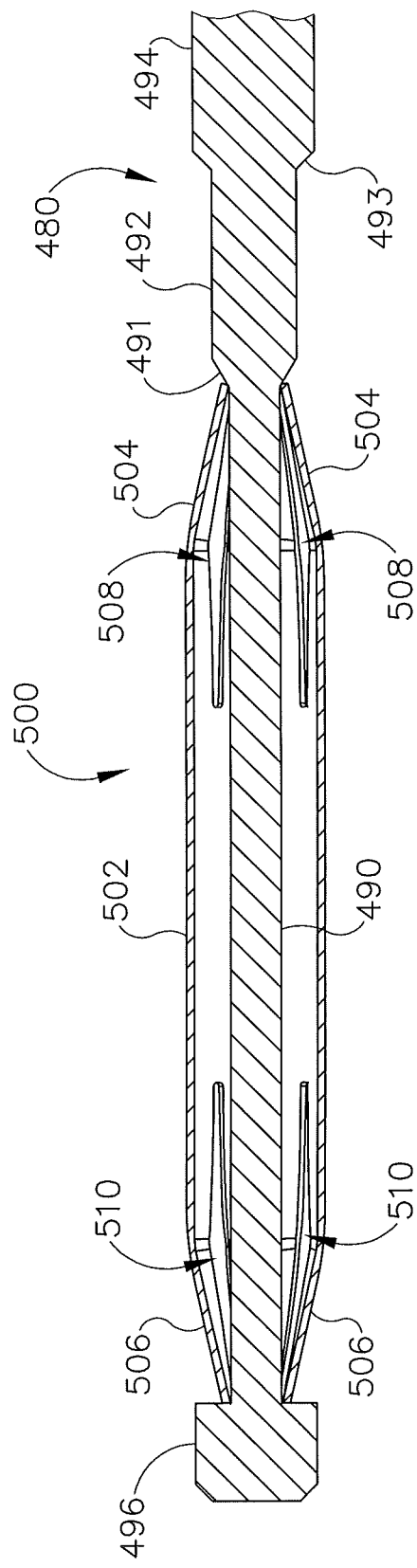
FIG. 21 depicts a cross-sectional side elevational view of the proximal portion of the piercer and clutch of FIG. 19.
Figure 22:
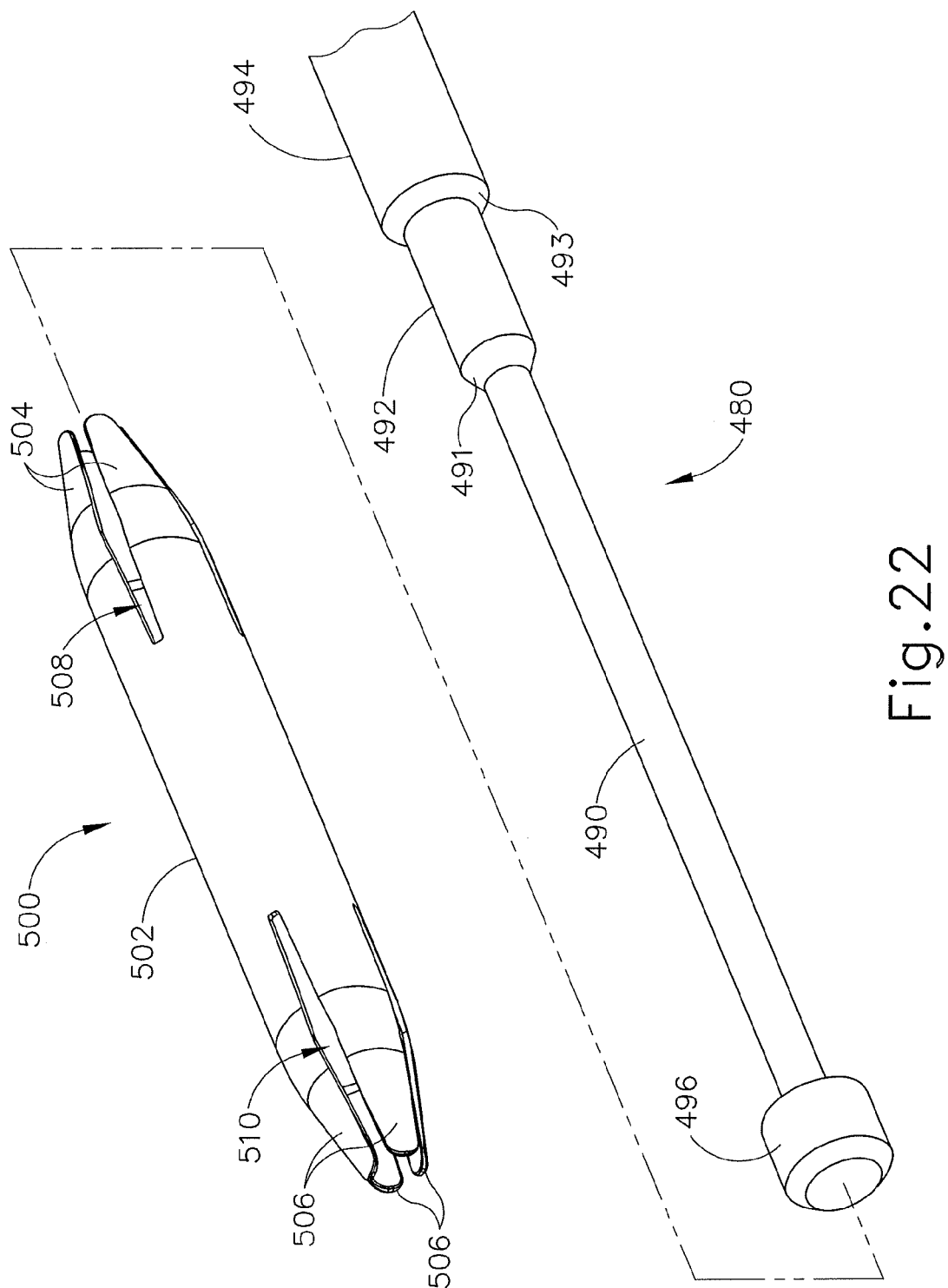
FIG. 22 depicts an exploded perspective view of the proximal portion of the piercer and clutch of FIG. 19.
Figure 23:
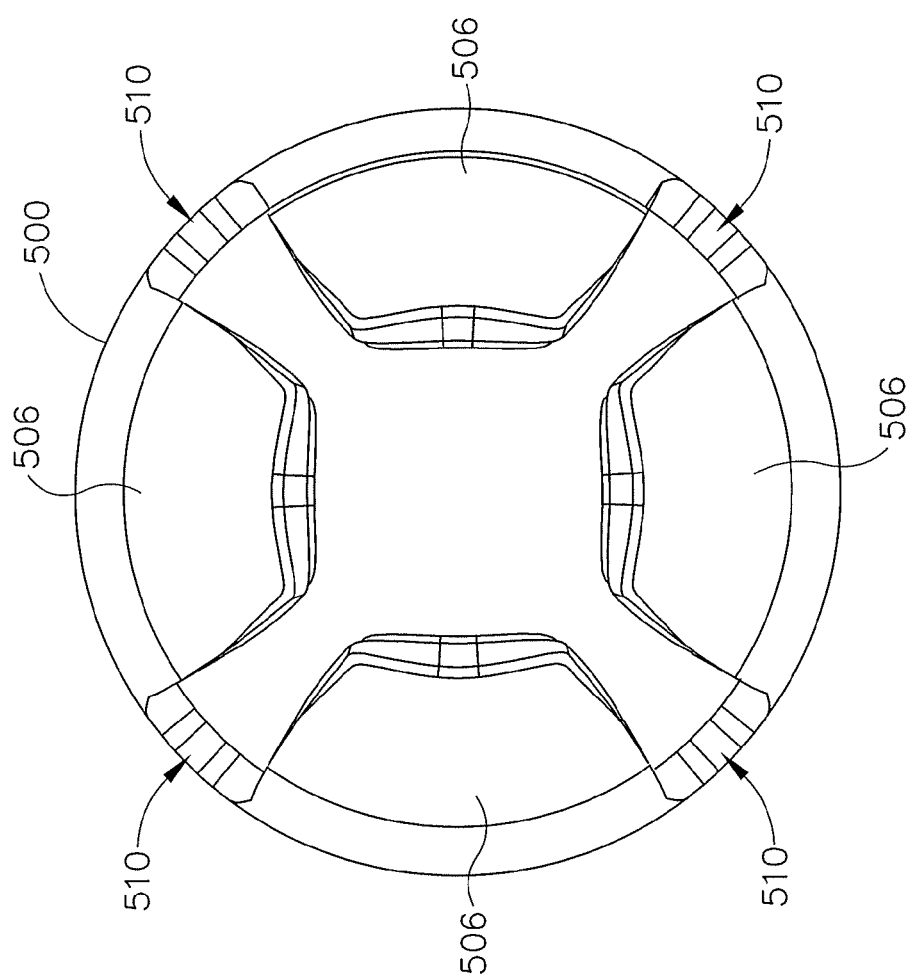
FIG. 23 depicts a front elevational view of the clutch of FIG. 19.

As best seen in FIGS. 21 and 22, a proximal portion of piercer (480) comprises a first cylindrical portion (490), a second cylindrical portion (492), and a third cylindrical portion (494) each having a larger diameter than the former. In particular, third cylindrical portion (494) of the present example has a larger diameter than second cylindrical portion (492), and second cylindrical portion (492) has a larger diameter than first cylindrical portion (490). Second cylindrical portion (492) is located distally of first cylindrical portion (490), and third cylindrical portion (494) is located distally of second cylindrical portion (492). A first chamfered or conical portion (491) provides for transition between a distal end of first cylindrical portion (490) and a proximal end of second cylindrical portion (492). A second chamfered or conical portion (493) provides for transition between a distal end of second cylindrical portion (492) and a proximal end of third cylindrical portion (494). The proximal portion of piercer (480) further comprises a proximal stop (496) located at a proximal end of first cylindrical portion (490). As best seen in FIG. 21, a stepped transition presents a distal face (497) between the proximal end of first cylindrical portion (490) and proximal stop (496). In the present example of piercer (480), an outer diameter of proximal stop (496) is approximately equal to the diameter of third cylindrical portion (494).

Figure 19:
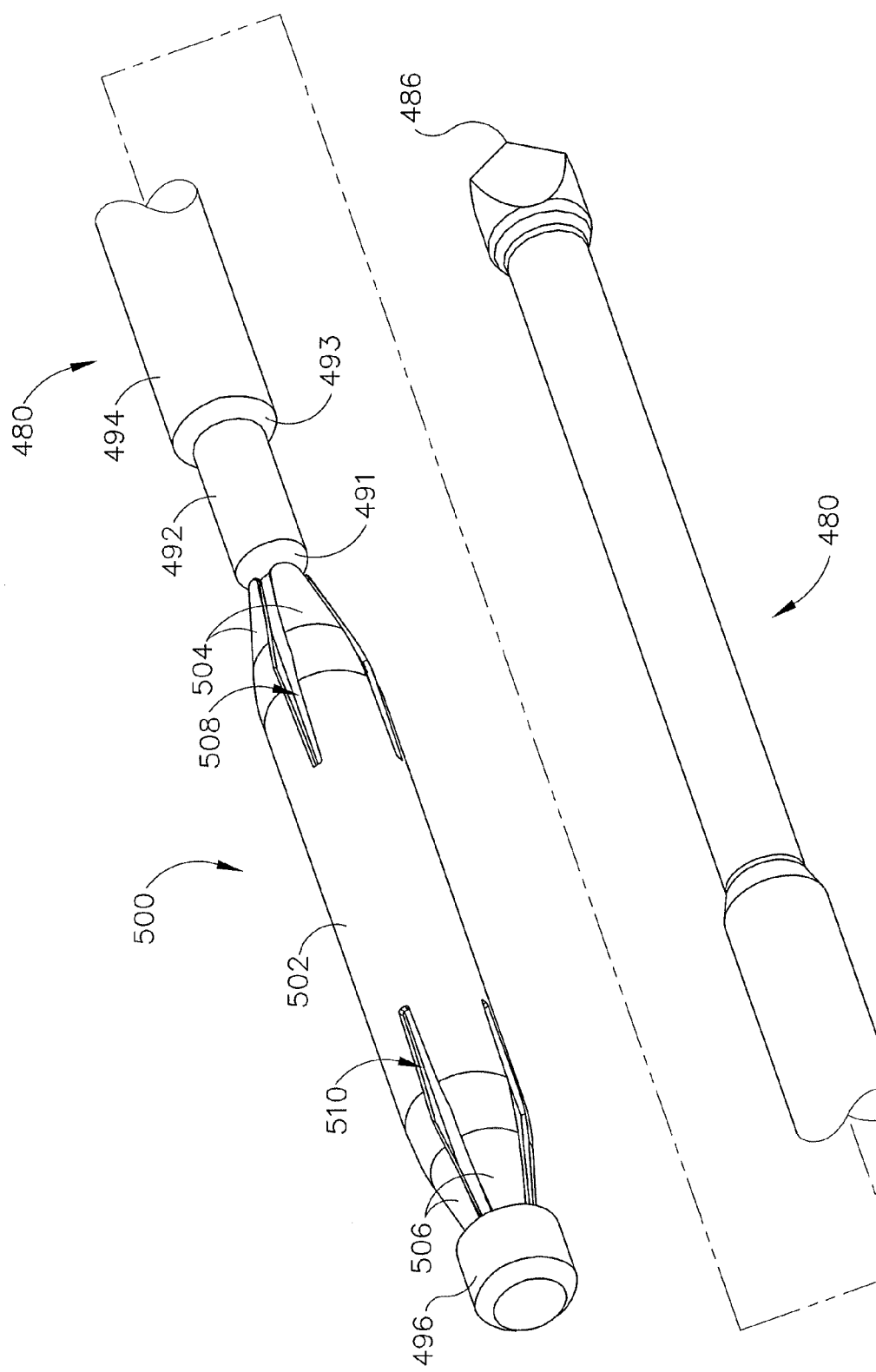
FIG. 19 depicts a perspective view of a piercer and clutch of the shaft assembly of FIG. 16.
Figure 20:
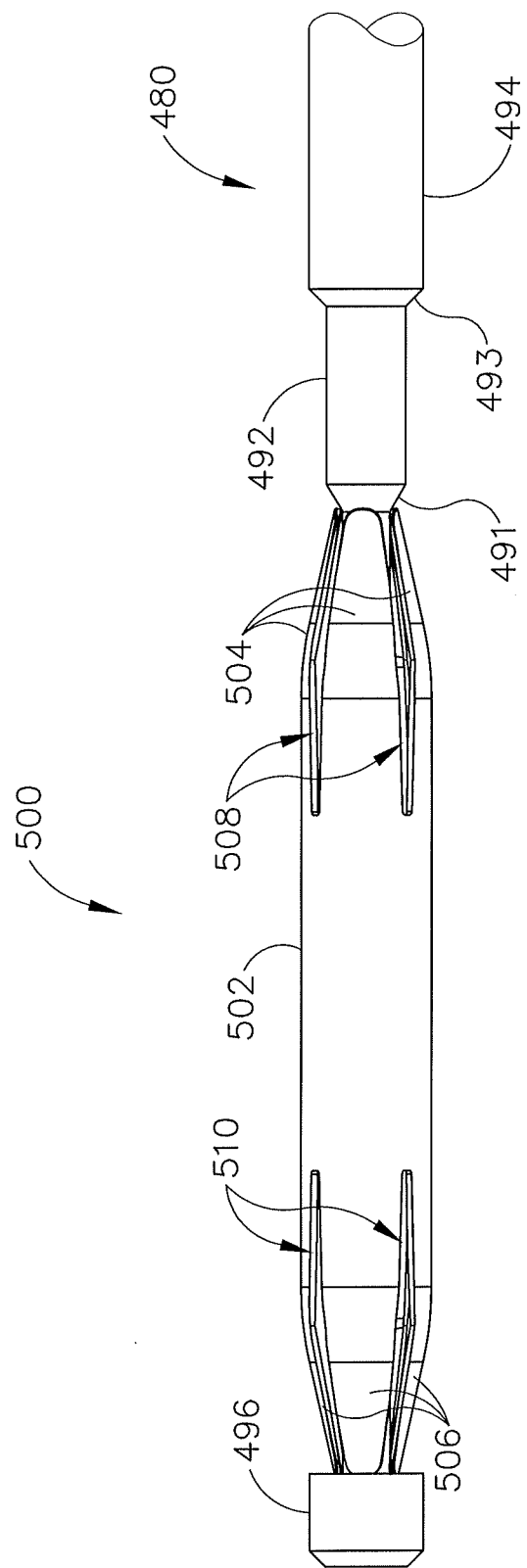
FIG. 20 depicts a side elevational view of a proximal portion of the piercer and clutch of FIG. 19.

As best seen in FIGS. 19-23, clutch (500) of the present example comprises a hollow cylindrical body (502) having a first plurality of generally flexible leaves (504) extending distally from a distal end of cylindrical body (502) and a second plurality of generally flexible leaves (506) extending proximally from a proximal end of cylindrical body (502). Flexible leaves (504, 506) are separated by longitudinally extending gaps (508, 510). Flexible leaves (504, 506) are resiliently biased to assume the inwardly deflected positioning as best seen in FIGS. 20 and 21; but are operable to flex outwardly from this positioning as will be described in greater detail below.

As shown in FIGS. 19-21, in a "home" position, clutch (500) is positioned about first cylindrical portion (490). Clutch (500) is configured such that clutch (500) extends the length of first cylindrical portion (490) (i.e. substantially the length from proximal stop (496) to first conical portion (491)). Thus, as best seen in FIGS. 20 and 21, in the "home" position, the proximal tips of flexible leaves (506) engage distal face (497) of proximal stop (496). It should therefore be understood that in the "home" position, proximal stop (496) will prevent proximal translation of clutch (500) relative to piercer (480) and distal translation of piercer (480) relative to clutch (500). Also in the "home" position, distal tips of flexible leaves (504) engage the exterior surface of first cylindrical portion (490) at a proximal base of first conical portion (491). It should therefore be understood that in the "home" position, conical portion (491) will inhibit distal translation of clutch (500) relative to piercer (480) and proximal translation of piercer (480) relative to clutch (500) unless a force is applied to clutch (500) and/or piercer (480) sufficient to overcome the resilient bias of flexible leaves (504) such that flexible leaves (504) spread to accommodate the diameter of first conical portion (491) and/or second cylindrical portion (492). Thus, it should be understood that upon such a sufficient force being applied to clutch (500) and/or piercer (480), flexible leaves (504) spread to accommodate the diameter of first conical portion (491) and/or second cylindrical portion (492) such that clutch (500) is able to move distally relative to piercer (480) and such that piercer (480) is able to move proximally relative to clutch (500).

Figure 24A:
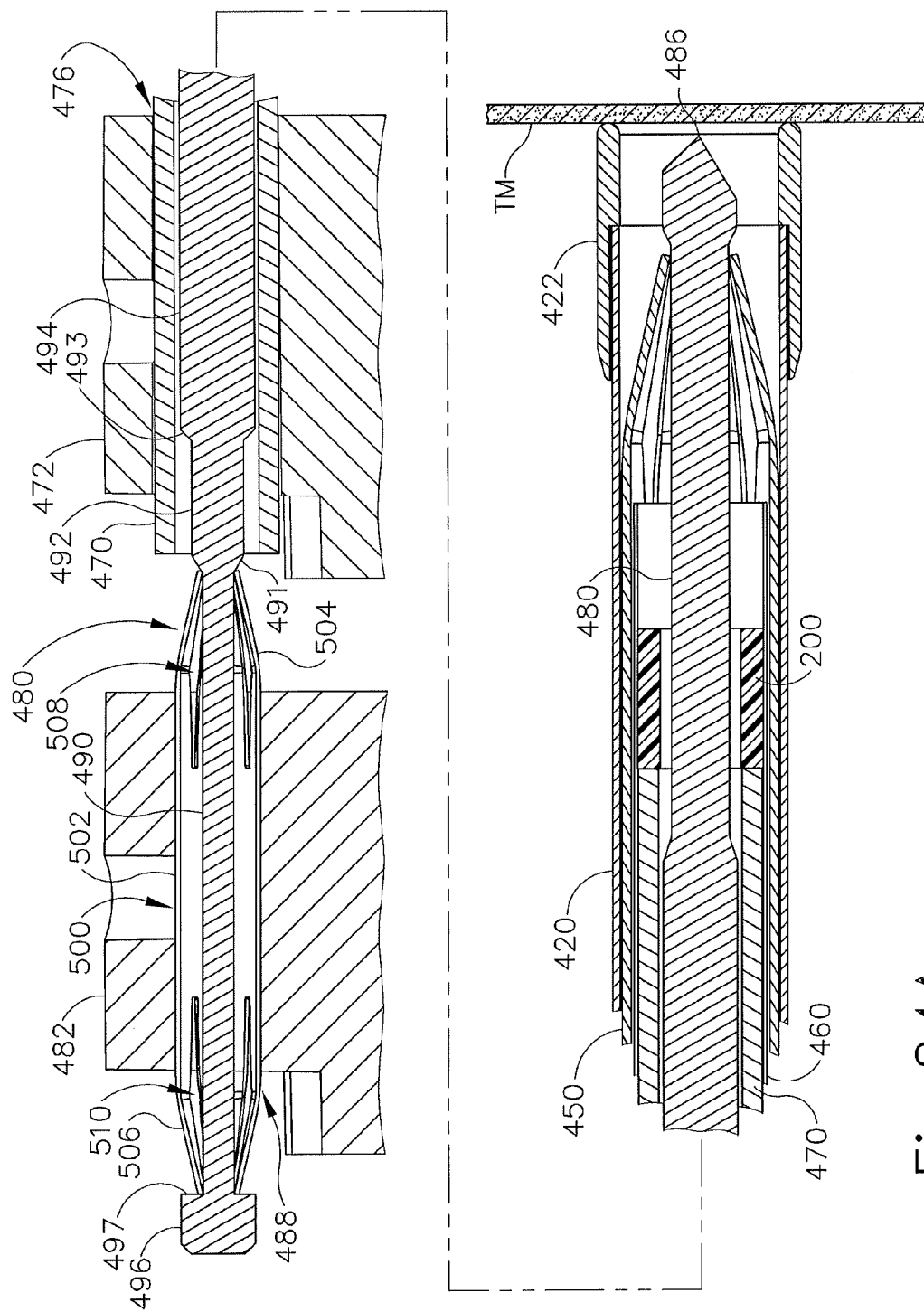
FIG. 24A depicts a cross-sectional side elevational view of the shaft assembly of FIG. 16, with a follower, the piercer of FIG. 19, and the clutch of FIG. 19 in a first longitudinal position.
Figure 24C:
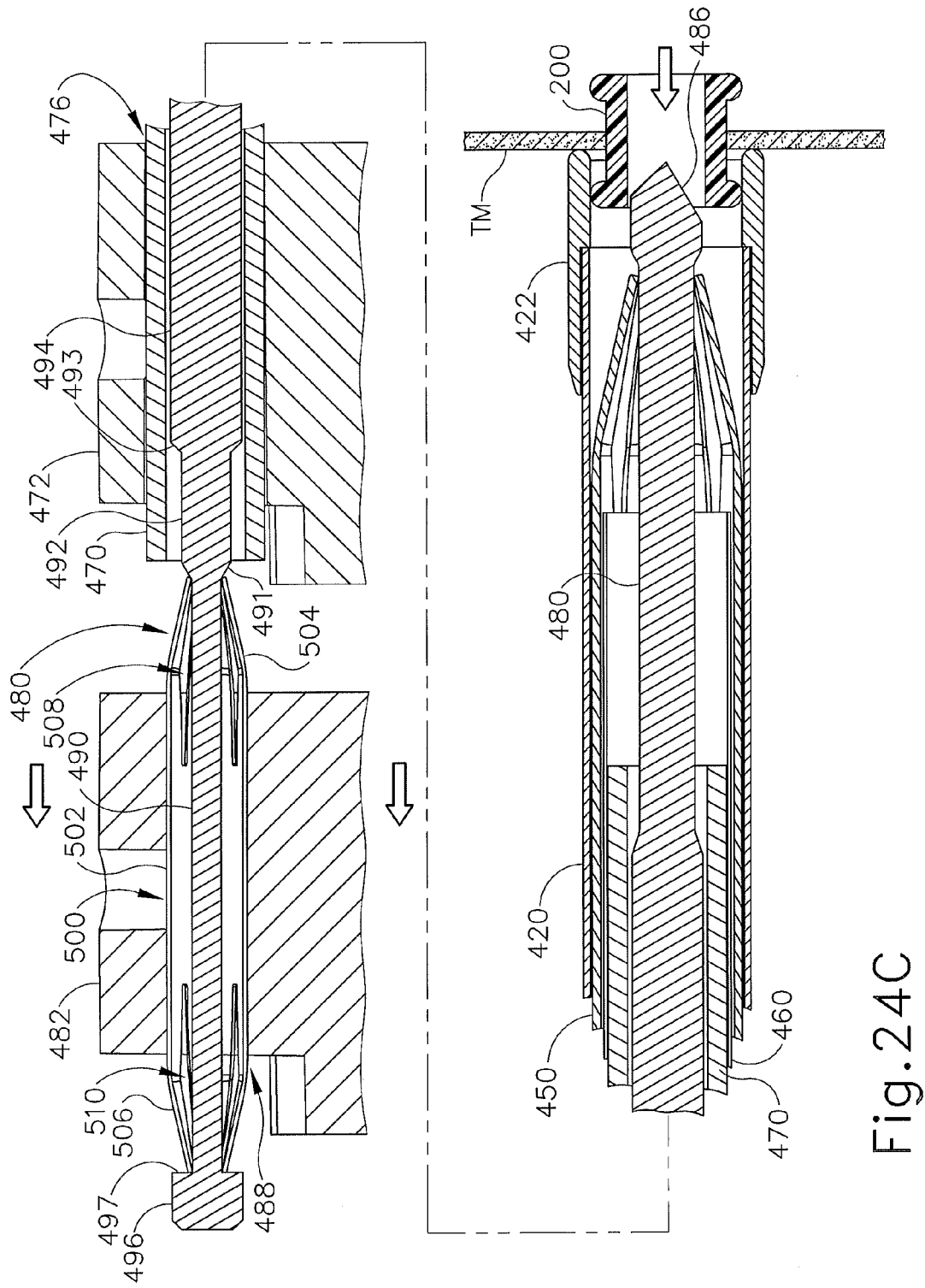
FIG. 24C depicts a cross-sectional side elevational view of the shaft assembly of FIG. 16, with the follower of FIG. 24A, the piercer of FIG. 19, and the clutch of FIG. 19 retracted proximally to the first longitudinal position with a PE tube disposed within a tympanic membrane.

FIGS. 24A-24C depict a sequence of normal operation that occurs upon rotation of camshaft (430) from a home position to an actuated position. FIG. 24A shows the positioning of tubes (450, 460, 470), piercer (480), and PE tube (200) within cannula (420) before camshaft (430) starts rotating from a home position. As shown, followers (472, 482) are spaced apart from one another. Pusher tube (470) is fixedly secured within a through-bore (476) of cam follower (472) such that translation of cam follower (472) causes concurrent translation of pusher tube (470). Piercer (480) is slidably disposed within pusher tube (470) such that piercer (480) is operable to translate within and relative to pusher tube (470). Piercer (480) is selectively slidably coupled within a through-bore (488) of cam follower (482) via clutch (500) such that translation of cam follower (482) causes concurrent translation of clutch (500) and piercer (480). (As discussed above, and as will be discussed in more detail below, however, if a force is applied to clutch (500) and/or piercer (480) sufficient to overcome the resilient bias of flexible leaves (504), follower (482) is configured to translate independently of piercer (480).) As shown in FIG. 24B, as follower (482) and clutch (500) translate distally, piercer (480) translates distally as well and contacts the tympanic membrane (TM) so as to pierce the tympanic membrane (TM). The tympanic membrane (TM) resists piercer (480) with a force insufficient to overcome the resilient bias of flexible leaves (504) such that as follower (482) and clutch (500) are further translated distally, piercer (480) continues to translate distally thereby piercing tympanic membrane (TM). After having deployed PE tube (200) within the tympanic membrane (TM) as discussed above with reference to PETDD (100), follower (482) is translated proximally so as to cause concurrent proximal translation of piercer (480) via engagement between flexible leaves (506) of clutch (500) and proximal stop (496) of piercer (480) as shown in FIG. 24C.

Figure 25A:
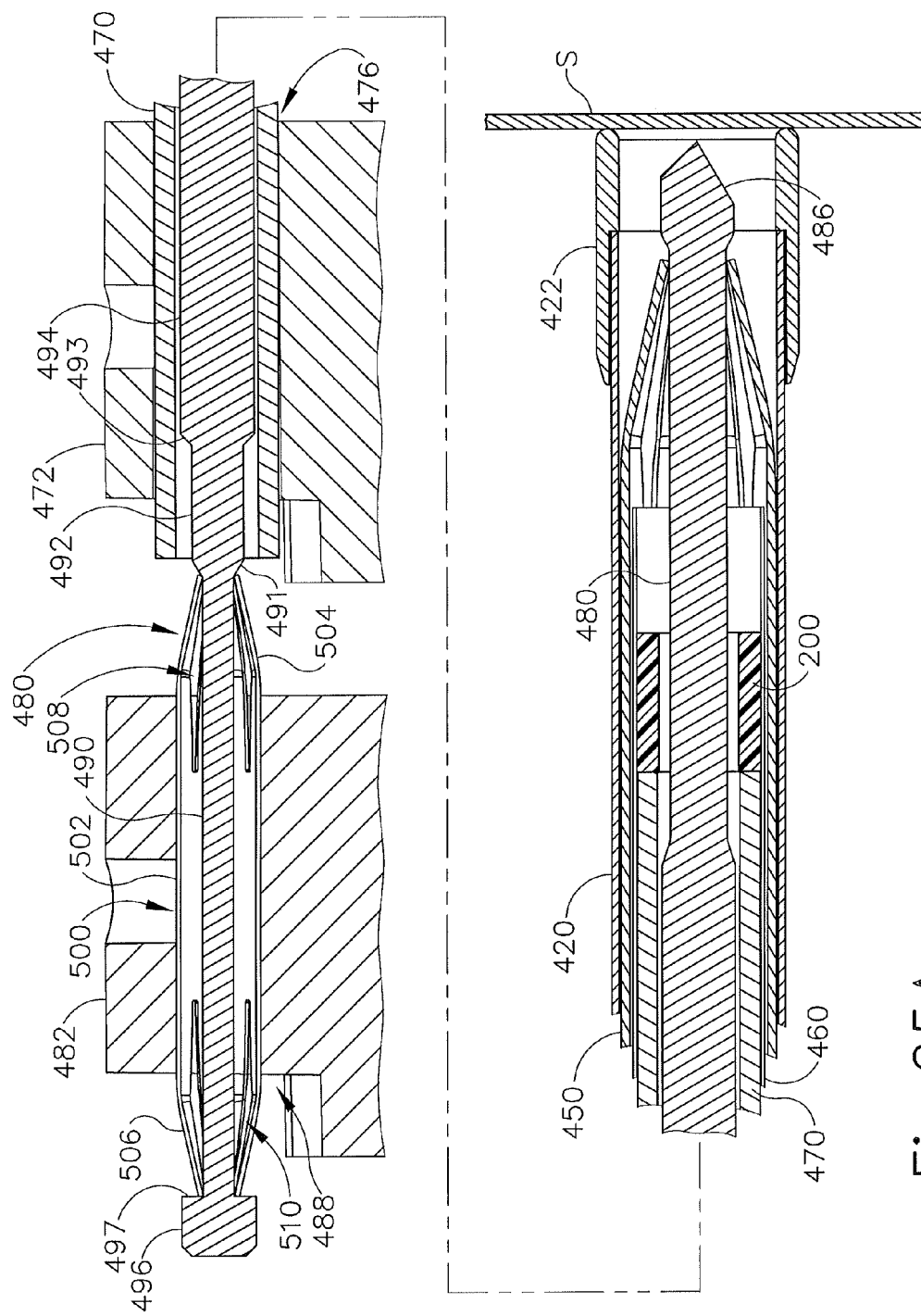
FIG. 25A depicts a cross-sectional side elevational view of the shaft assembly of FIG. 16, with a follower, the piercer of FIG. 19, and the clutch of FIG. 19 in a first longitudinal position.
Figure 25B:
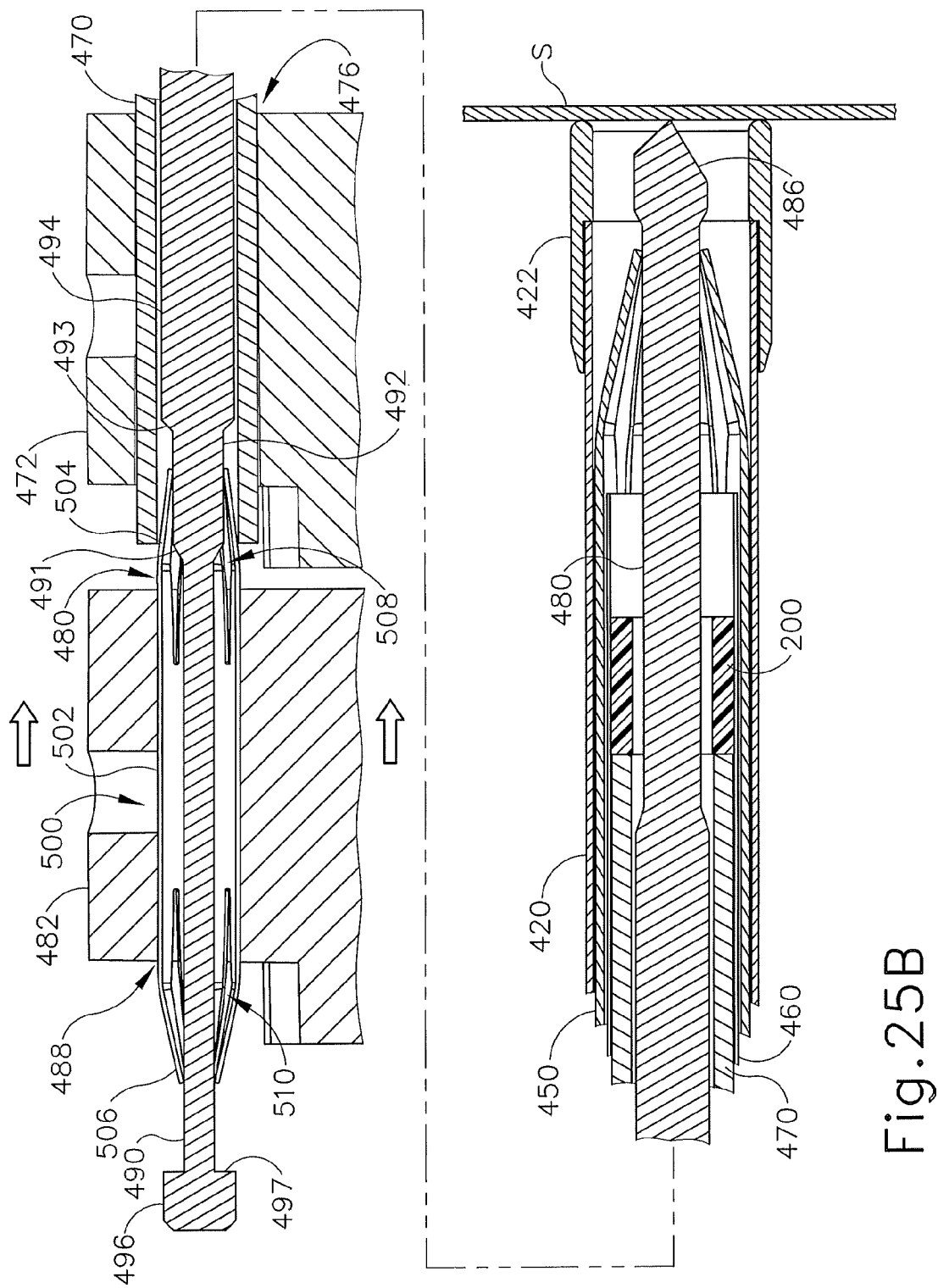
FIG. 25B depicts a cross-sectional side elevational view of the shaft assembly of FIG. 16, with the follower of FIG. 25A and the clutch of FIG. 19 moved distally to a second longitudinal position, and with the piercer of FIG. 19 remaining in the first longitudinal position.
Figure 25C:
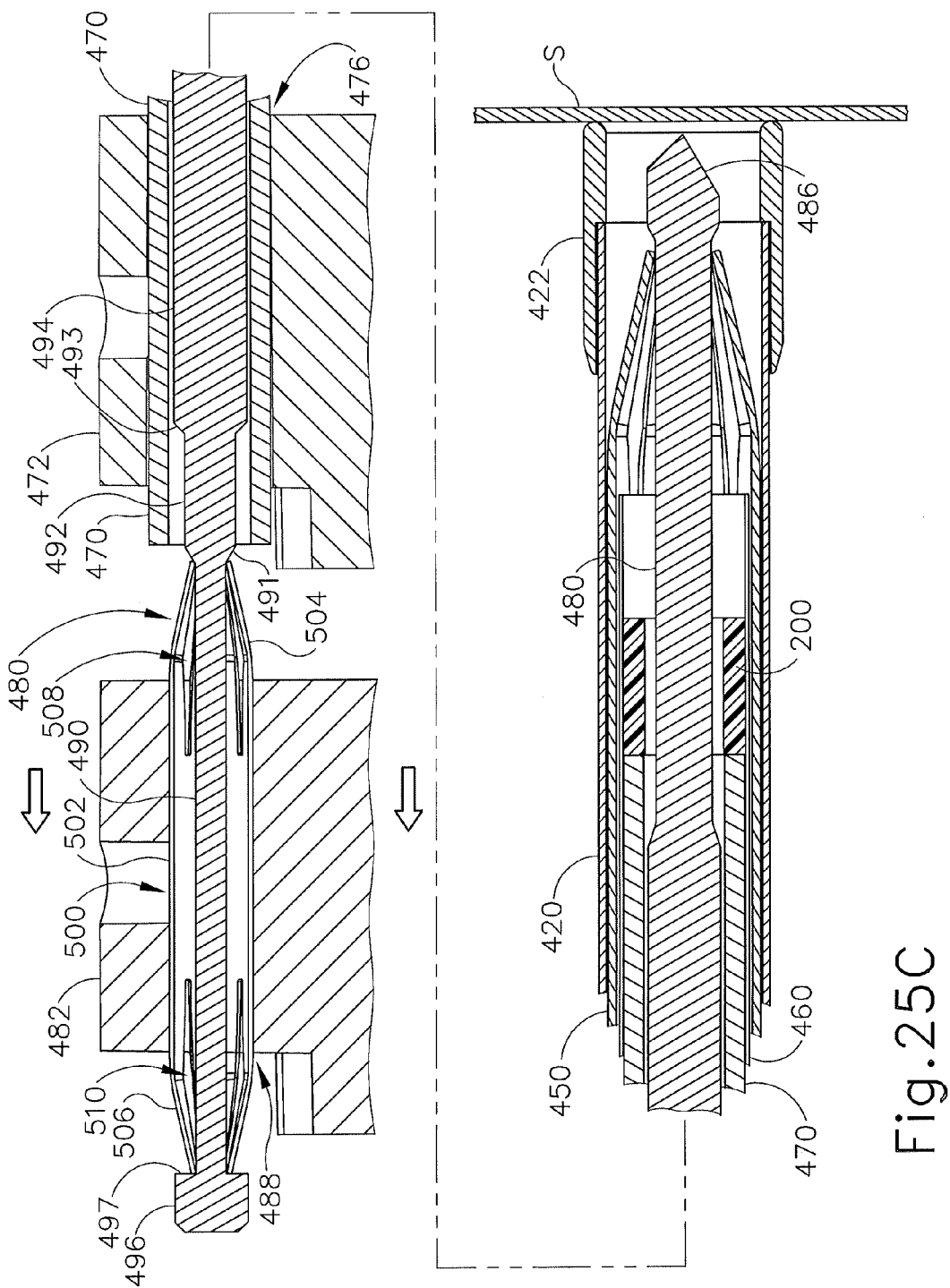
FIG. 25C depicts a cross-sectional side elevational view of the shaft assembly of FIG. 16, with the follower of FIG. 25A and the clutch of FIG. 19 retracted proximally to the first longitudinal position, and with the piercer of FIG. 19 remaining in the first longitudinal position.

FIGS. 25A-25C depict a sequence of operation that occurs upon rotation of camshaft (130) from a home position to an actuated position in which piercer (480) comes into contact with a surface not intended to be pierced (S). Surface (S) may include skin, bone, and/or any other kind of structure or material that has sufficiently greater strength or thickness than tympanic membrane (TM). Such surface (S) may be located within a patient's ear, for example a structure in the middle ear, medial to the tympanic membrane; or may be located outside a patient's ear. FIG. 25A shows the positioning of tubes (450, 460, 470), piercer (480), and PE tube (200) within cannula (420) before camshaft (430) starts rotating from a home position. As shown, followers (472, 482) are spaced apart from one another. Pusher tube (470) is fixedly secured within of cam follower (472) as discussed above. Piercer (480) is selectively slidably secured within cam follower (482) as discussed above. As shown in FIG. 25B, as follower (482) and clutch (500) translate distally, piercer (480) translates distally as well and contacts surface (S). Surface (S) resists piercer (480) with a force sufficient to overcome the resilient bias of flexible leaves (504) such that as follower (482) and clutch (500) are further translated distally, flexible leaves (504) flex outwardly to accommodate first conical portion (491) and second cylindrical portion (492) such that clutch (500) and follower (482) may translate distally relative to piercer (480). Thus, as shown in FIG. 25B, distal translation of follower (482) is not communicated to piercer (480) such that piercer (480) does not translate further distally and pierce surface (S). The drive assembly continues its normal operational sequence of distal advancement of tubes (450, 460, 470) while piercer (480) remains stationary. In some instances, tubes (450, 460, 470) may tend to push PETDD (400) proximally when tubes (450, 460, 470) drive distally into surface (S) while piercer (480) remains stationary. As drive assembly begins the sequence of driving components proximally, follower (482) and clutch (500) are translated proximally independent of piercer (480) until flexible leaves (506) of clutch (500) engage proximal stop (496) of piercer (480) at which point proximal translation of follower (482) will be communicated to piercer (480) as shown in FIG. 25C. As follower (482) and clutch (500) translate proximally, flexible leaves (504) contract along first conical portion (491) to the diameter of first cylindrical portion (490) due to the resilient bias of flexible leaves (504). In some versions, PETDD (400) is ready to fire again at this stage, as the movable components are reset to the initial state shown in FIG. 25A.

Figure 26A:
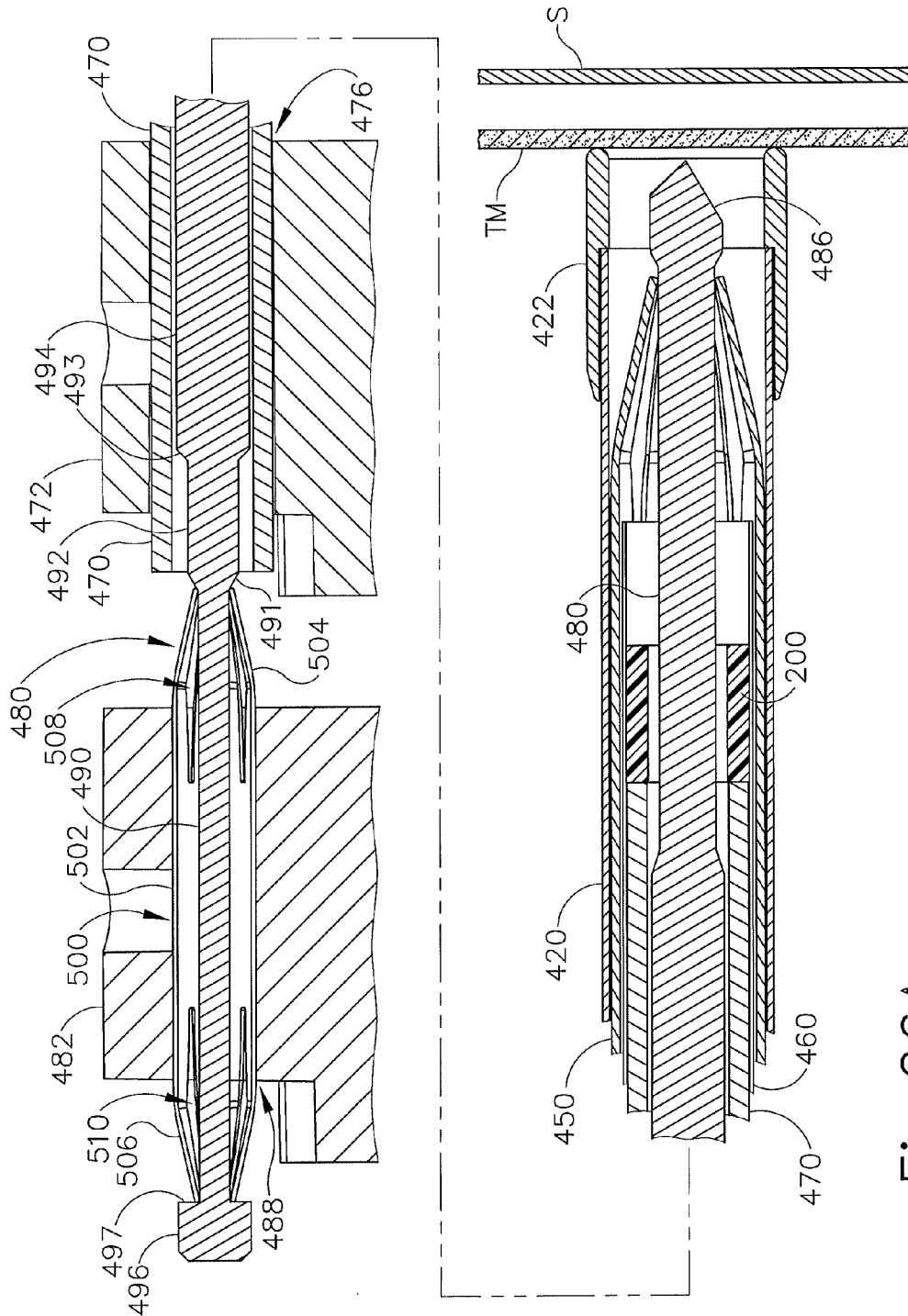
FIG. 26A depicts a cross-sectional side elevational view of the shaft assembly of FIG. 16, with a follower, the piercer of FIG. 19, and the clutch of FIG. 19 in a first longitudinal position.
Figure 26B:
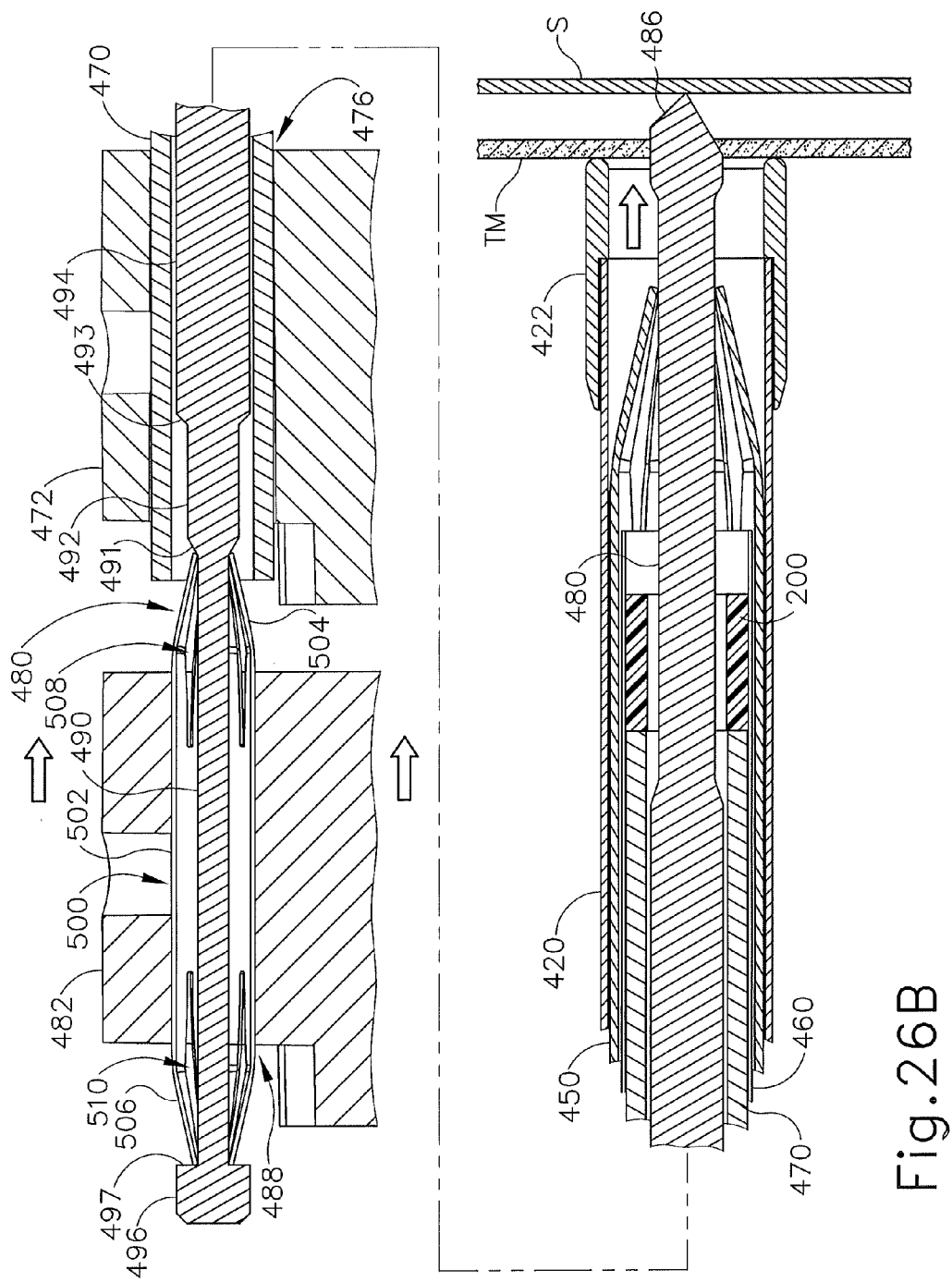
FIG. 26B depicts a cross-sectional side elevational view of the shaft assembly of FIG. 16, with the follower of FIG. 26A, the piercer of FIG. 19, and the clutch of FIG. 19 moved distally to a second longitudinal position so as to pierce a tympanic membrane.
Figure 26C:
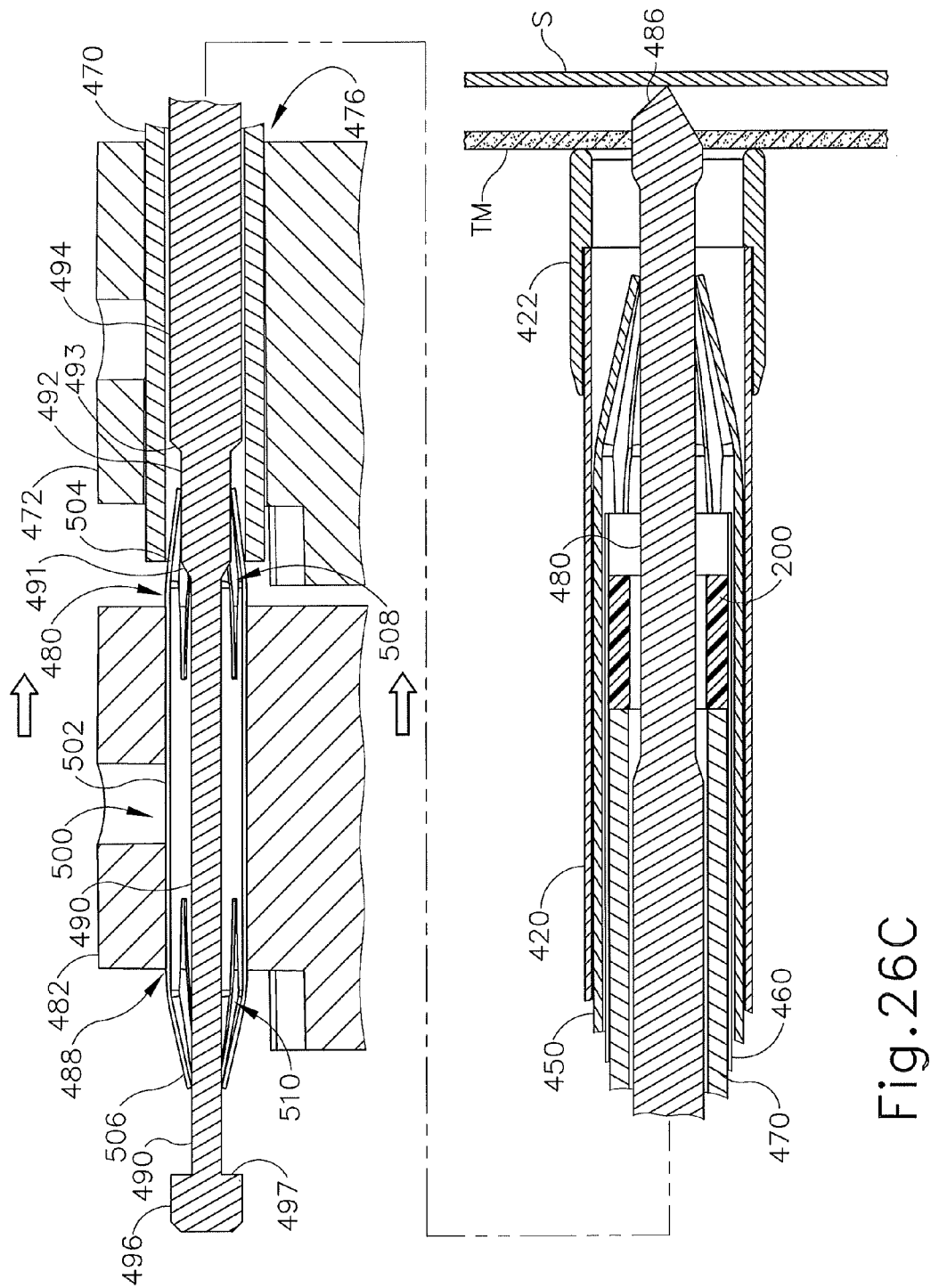
FIG. 26C depicts a cross-sectional side elevational view of the shaft assembly of FIG. 16, with the follower of FIG. 26A and the clutch of FIG. 19 moved distally to a third longitudinal position, and with the piercer of FIG. 19 remaining in the second longitudinal position.
Figure 26D:
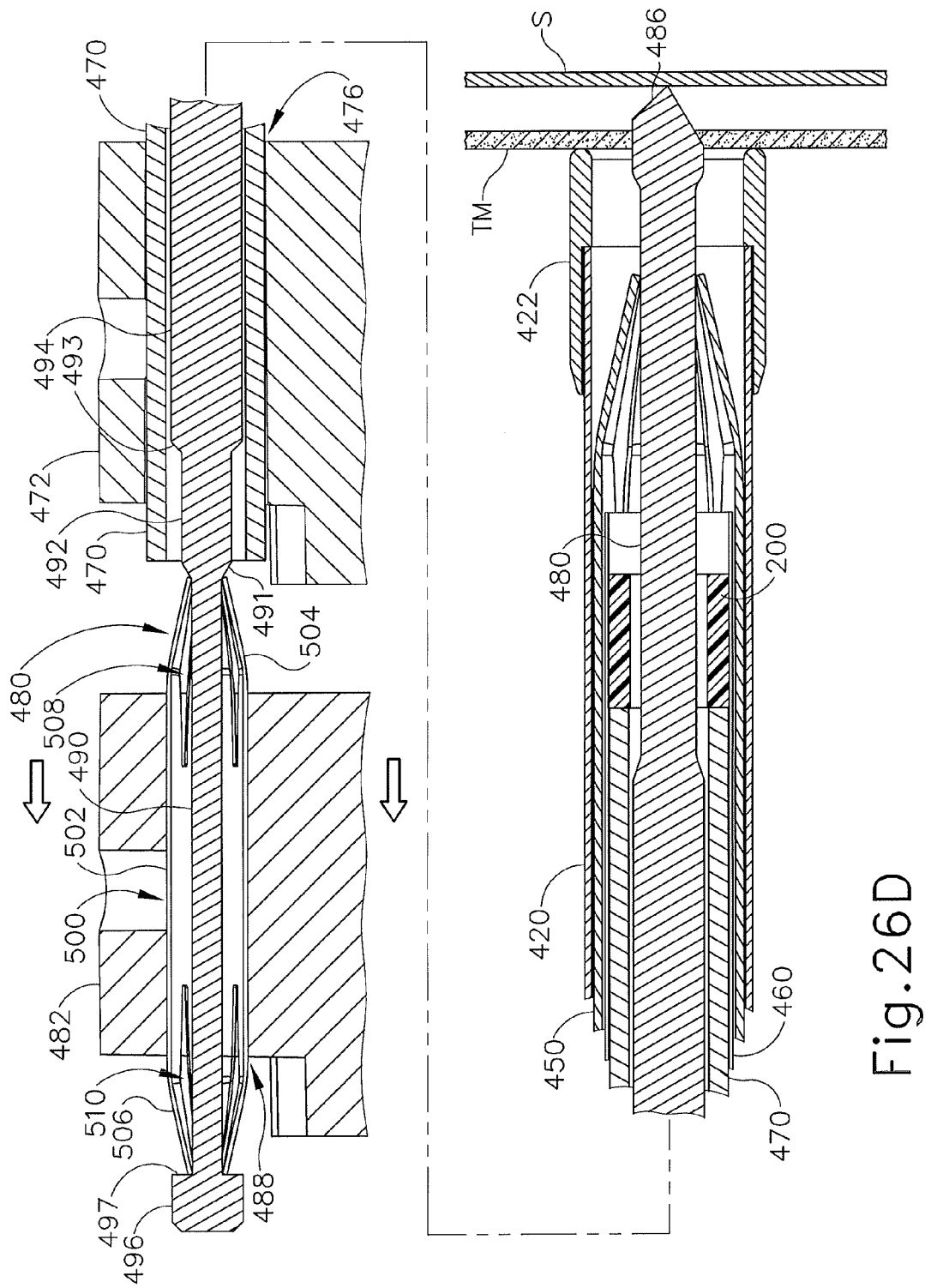
FIG. 26D depicts a cross-sectional side elevational view of the shaft assembly of FIG. 16, with the follower of FIG. 26 and the clutch of FIG. 19 retracted proximally to the second longitudinal position, and with the piercer of FIG. 19 remaining in the second longitudinal position.
Figure 26E:
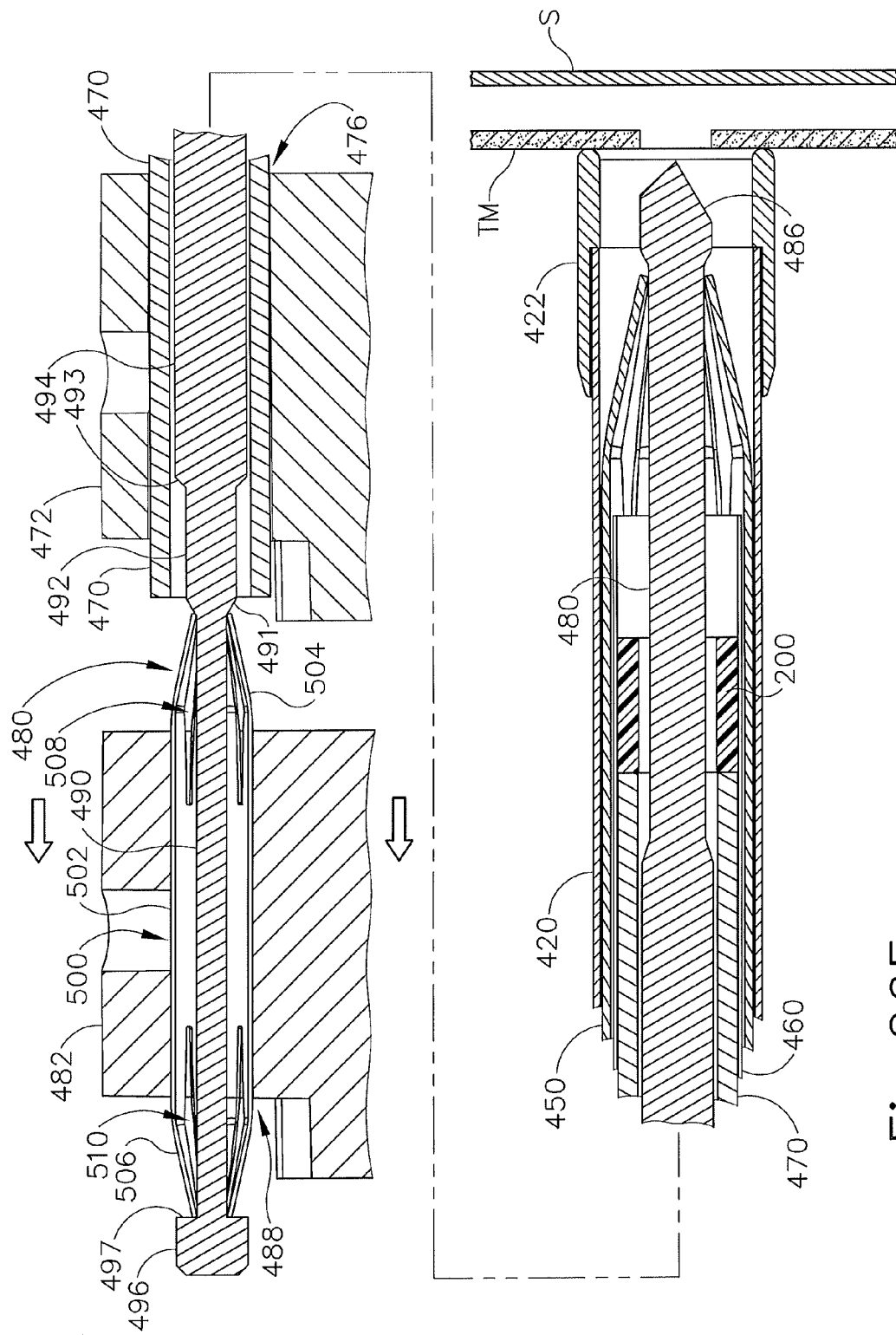
FIG. 26E depicts a cross-sectional side elevational view of the shaft assembly of FIG. 16, with the follower of FIG. 26A, the piercer of FIG. 19, and the clutch of FIG. 19 retracted proximally to the first longitudinal position.

FIGS. 26A-26E depict a sequence of operation that occurs upon rotation of camshaft (130) from a home position to an actuated position in which piercer (480) comes into contact with a surface not intended to be pierced (S) after piercing the tympanic membrane (TM). FIG. 26A shows the positioning of tubes (450, 460, 470), piercer (480), and PE tube (200) within cannula (420) before camshaft (430) starts rotating from a home position. As shown, followers (472, 482) are spaced apart from one another. Pusher tube (470) is fixedly secured within of cam follower (472) as discussed above. Piercer (480) is selectively slidably secured within cam follower (482) as discussed above. As shown in FIG. 26B, as follower (482) and clutch (500) translate distally, piercer (480) translates distally as well and contacts the tympanic membrane (TM) so as to pierce the tympanic membrane (TM). The tympanic membrane (TM) resists piercer (480) with a force insufficient to overcome the resilient bias of flexible leaves (504) such that as follower (482) is further translated distally, piercer (480) continues to translate distally thereby piercing the tympanic membrane (TM). As shown in FIG. 25C, as follower (482) and clutch (500) translate further distally, piercer (480) translates distally as well and contacts surface (S). Surface (S) resists piercer (480) with a force sufficient to overcome the resilient bias of flexible leaves (504) such that as follower (482) and clutch (500) are further translated distally, flexible leaves (504) flex outwardly to accommodate first conical portion (491) and second cylindrical portion (492) such that clutch (500) and follower (482) may translate distally relative to piercer (480). Thus, as shown in FIG. 25C, distal translation of follower (482) is not communicated to piercer (480) such that piercer (480) does not pierce surface (S). As drive assembly begins the sequence of driving components proximally, follower (482) and clutch (500) are translated proximally independent of piercer (480) until flexible leaves (506) of clutch (500) engage proximal stop (496) of piercer (480) (FIG. 26D) at which point proximal translation of follower (482) will be communicated to piercer (480) as shown in FIG. 26E. As follower (482) and clutch (500) translate proximally, flexible leaves (504) contract along first conical portion (491) to the diameter of first cylindrical portion (490) due to the resilient bias of flexible leaves (504). In some versions, PETDD (400) is ready to fire again at this stage, as the movable components are reset to the initial state shown in FIG. 25A.

The force required to overcome the resilient bias of flexible leaves (504), to thereby force the flexible leaves (504) spread apart to accommodate the diameter of first conical portion (491) and/or second cylindrical portion (492), may be manipulated or fine tuned by changing various parameters, including but not limited to the following: the material of clutch (500); the surface finish of first conical portion (491), second cylindrical portion (492), and/or flexible leaves (504); the angle of first conical portion (491) relative to first cylindrical portion (490); and/or other characteristics of piercer (480) and/or clutch (500) as will be understood by one of ordinary skill in the art. It should also be appreciated that, although clutch (500) of the present example provides selective communication of movement to piercer (480) via flexible leaves (504, 506), clutch (500) may additionally or alternatively comprise magnets, buckling elements, breakaway components, and/or other kinds of features to provide for selective communication of movement from cam follower (482) to piercer (480).

The foregoing components, features, and operabilities of PETDD (400) are merely illustrative examples. A PETDD (400) may include various other features in addition to or in lieu of those described above. By way of example only, any of the devices herein may also include one or more of the various features disclosed in any of the various references that are incorporated by reference herein. Some additional merely illustrative variations of PETDD (400) will be described in greater detail below, while other variations of PETDD (400) will be apparent to those of ordinary skill in the art in view of the teachings herein.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In some instances, the device is sterilized using conventional ethylene oxide sterilization techniques and systems. In some other instances, the device is placed in a closed and sealed container, such as a plastic or TYVEK bag; and the container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, steam, etc.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An instrument, comprising:
   (a) a shaft assembly including a translatable piercing element;
   (b) a drive assembly including a translatable driver; and
   (c) a clutch comprising a body and a first plurality of flexible leaves and a second plurality of flexible leaves extending from the body, the clutch removably coupling the translatable piercing element with the translatable driver such that the translatable driver can drive the translatable piercing element via the clutch,
   wherein in response to a threshold resistance force being imposed on the translatable piercing element, the clutch decouples the translatable piercing element from the translatable driver and the translatable driver can translate relative to the translatable piercing element.

2. The instrument of claim 1, wherein the clutch is fixedly secured to the translatable driver.

3. The instrument of claim 1, wherein the clutch is disposed within a through-bore of the translatable driver.

4. The instrument of claim 1, wherein the flexible leaves of at least one of the first plurality of flexible leaves and the second plurality of flexible leaves are resiliently biased inwardly.

5. The instrument of claim 1, wherein the first plurality of flexible leaves extends distally from a distal end of the body of the clutch and the second plurality of flexible leaves extends proximally from a proximal end of the body of the clutch.

6. The instrument of claim 1, wherein the translatable piercing element comprises:
   (i) a first cylindrical portion having a first diameter;
   (ii) a second cylindrical portion having a second diameter; and
   (iii) a conical portion between the first cylindrical portion and the second cylindrical portion, wherein the conical portion provides for transition between the first diameter and the second diameter.

7. The instrument of claim 6, wherein the first diameter is smaller than the second diameter.

8. The instrument of claim 6, wherein the clutch is configured to engage at least one of the first cylindrical portion and the conical portion of the translatable piercing element.

9. The instrument of claim 8, wherein the translatable driver is configured to drive the translatable piercing element via the clutch when the clutch is engaged with the at least one of the first cylindrical portion and the conical portion of the translatable piercing element.

10. The instrument of claim 6, wherein the clutch is configured to disengage at least one of the first cylindrical portion and the conical portion of the translatable piercing element in response to the threshold resistance force being imposed on the translatable piercing element.

11. The instrument of claim 10, wherein the translatable driver is configured to translate relative to the translatable piercing element in response to disengagement of the clutch from the at least one of the first cylindrical portion and the conical portion of the translatable piercing element.

12. The instrument of claim 6, wherein the first cylindrical portion has a length and the clutch extends substantially the length of the first cylindrical portion of the translatable piercing element.

13. The instrument of claim 1, wherein the translatable piercing element comprises a proximal stop configured to prevent proximal translation of the clutch relative to the translatable piercing element and distal translation of the translatable piercing element relative to the clutch.

14. An instrument, comprising:
(a) a shaft assembly including a translatable piercing element, the translatable piercing element comprising:
(i) a first cylindrical portion having a first diameter and a length;
(ii) a second cylindrical portion having a second diameter; and
(iii) a conical portion between the first cylindrical portion and the second cylindrical portion, wherein the conical portion provides for transition between the first diameter and the second diameter;
(b) a drive assembly including a translatable driver; and
(c) a clutch extending substantially the length of the first cylindrical portion of the translatable piercing element, the clutch removably coupling the translatable piercing element with the translatable driver such that the translatable driver can drive the translatable piercing element via the clutch,
wherein in response to a threshold resistance force being imposed on the translatable piercing element, the clutch decouples the translatable piercing element from the translatable driver and the translatable driver can translate relative to the translatable piercing element.

15. The instrument of claim 14, wherein the first diameter is smaller than the second diameter.

16. The instrument of claim 14, wherein the clutch is configured to engage at least one of the first cylindrical portion and the conical portion of the translatable piercing element.

17. The instrument of claim 16, wherein the translatable driver is configured to drive the translatable piercing element via the clutch when the clutch is engaged with the at least one of the first cylindrical portion and the conical portion of the translatable piercing element.

18. The instrument of claim 14, wherein the clutch is configured to disengage at least one of the first cylindrical portion and the conical portion of the translatable piercing element in response to the threshold resistance force being imposed on the translatable piercing element.

19. The instrument of claim 18, wherein the translatable driver is configured to translate relative to the translatable piercing element in response to disengagement of the clutch from the at least one of the first cylindrical portion and the conical portion of the translatable piercing element.

20. The instrument of claim 14, wherein the translatable piercing element comprises a proximal stop configured to prevent proximal translation of the clutch relative to the translatable piercing element and distal translation of the translatable piercing element relative to the clutch.

21. An instrument, comprising:
(a) a shaft assembly including a translatable piercing element, the translatable piercing element comprising a proximal stop;
(b) a drive assembly including a translatable driver; and
(c) a clutch removably coupling the translatable piercing element with the translatable driver such that the translatable driver can drive the translatable piercing element via the clutch,
wherein in response to a threshold resistance force being imposed on the translatable piercing element, the clutch decouples the translatable piercing element from the translatable driver and the translatable driver can translate relative to the translatable piercing element, and wherein the proximal stop of the translatable piercing element is configured to prevent proximal translation of the clutch relative to the translatable piercing element and distal translation of the translatable piercing element relative to the clutch.

* * * * *